(12) United States Patent
Bocek et al.

(10) Patent No.: US 11,648,399 B2
(45) Date of Patent: May 16, 2023

(54) SENSING REFERENCE ELECTRODE FOR PERCUTANEOUS NEUROMODULATION TRIALS

(71) Applicant: Boston Scientific Neuromodulation Corporation, Valencia, CA (US)

(72) Inventors: Joseph M. Bocek, Seattle, WA (US); Michael X. Govea, Castaic, CA (US); Rosana Esteller, Santa Clarita, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 235 days.

(21) Appl. No.: 16/895,737

(22) Filed: Jun. 8, 2020

(65) Prior Publication Data

US 2020/0384271 A1 Dec. 10, 2020

Related U.S. Application Data

(60) Provisional application No. 62/859,430, filed on Jun. 10, 2019.

(51) Int. Cl.
*A61N 1/36* (2006.01)
*A61N 1/05* (2006.01)

(52) U.S. Cl.
CPC ....... *A61N 1/36132* (2013.01); *A61N 1/0502* (2013.01); *A61N 1/0551* (2013.01); *A61N 1/36017* (2013.01)

(58) Field of Classification Search
CPC .............. A61N 1/36132; A61N 1/0502; A61N 1/0551; A61N 1/36017; A61N 1/37241; A61N 1/372
See application file for complete search history.

(56) References Cited

U.S. PATENT DOCUMENTS

| | | | |
|---|---|---|---|
| 9,409,012 B2 | 8/2016 | Eidenschink et al. | |
| 10,016,607 B2 | 7/2018 | Min | |
| 2003/0199948 A1* | 10/2003 | Kokones | A61N 1/0551 607/117 |
| 2005/0203599 A1* | 9/2005 | Garabedian | A61N 1/0551 607/116 |
| 2013/0345777 A1* | 12/2013 | Feldman | A61N 1/3925 607/62 |
| 2018/0185651 A1 | 7/2018 | Astrom et al. | |

* cited by examiner

*Primary Examiner* — Mark W. Bockelman
(74) *Attorney, Agent, or Firm* — Schwegman Lundberg & Woessner, P.A.

(57) ABSTRACT

An example of an apparatus for percutaneously delivering neurostimulation energy to a patient and sensing from the patient using a test device placed externally to the patient is provided. The apparatus may include a stimulation lead, a sensing reference electrode, a sensing wire, and a connection system. The stimulation lead may be configured to be percutaneously introduced into the patient to place the one or more electrodes in the patient. The sensing reference electrode may be configured to be placed in the patient. The sensing wire may be connected to the sensing reference electrode and configured to be percutaneously introduced into the patient to place the sensing reference electrode in the patient. The connection system may be configured to mate the lead connector and the wire connector and to provide electrical connections between the lead connector and the test device and between the wire connector and the test device.

20 Claims, 11 Drawing Sheets

SENSING REFERENCE ELECTRODE FOR PERCUTANEOUS NEUROMODULATION TRIALS

CLAIM OF PRIORITY

This application claims the benefit of priority under 35 U.S.C. § 119(e) of U.S. Provisional Patent Application Ser. No. 62/859,430, filed on Jun. 10, 2019, which is herein incorporated by reference in its entirety.

TECHNICAL FIELD

This document relates generally to medical devices and more particularly to method and apparatus providing a percutaneous stimulation system with a sensing reference electrode for use during neuromodulation trials.

BACKGROUND

Neurostimulation, also referred to as neuromodulation, has been proposed as a therapy for a number of conditions. Examples of neurostimulation include Spinal Cord Stimulation (SCS), Deep Brain Stimulation (DBS), Peripheral Nerve Stimulation (PNS), and Functional Electrical Stimulation (FES). Implantable neurostimulation systems have been applied to deliver such a therapy. An implantable neurostimulation system can include an implantable neurostimulator, also referred to as an implantable pulse generator (IPG), and one or more implantable leads each including one or more electrodes. The implantable neurostimulator delivers neurostimulation energy through one or more electrodes placed on or near a target site in the nervous system. An external programming device is used to program the implantable neurostimulator with stimulation parameters controlling the delivery of the neurostimulation energy.

In one example, a temporary stimulation system is used to evaluate a neuromodulation therapy for a patient during a trial period for determination of whether an implantable neurostimulator is suitable for the patient. During the trial period, a trial lead is percutaneously placed with one end including electrodes in the patient and another end connected to an external trial stimulator GETS). Neurostimulation energy is delivered through the electrodes, and the delivery is controlled using stimulation parameters that specify spatial (where to stimulate), temporal (when to stimulate), and informational (patterns of stimulation directing the nervous system to respond as desired) aspects of a pattern of the neurostimulation energy. The stimulation parameters are evaluated and adjusted as needed by the patient and/or a care provider attending the patient, for therapeutic efficacy and efficiency as well as side-effects. It is desirable for the temporary stimulation system to emulate an implantable system that can be placed into the patient as a result of the evaluation of the neuromodulation therapy.

SUMMARY

An example (e.g., "Example 1") of an apparatus for percutaneously delivering neurostimulation energy to a patient and sensing from the patient using a test device placed externally to the patient is provided. The apparatus may include an elongate stimulation lead, a sensing reference electrode, an elongate sensing wire, and a connection system. The stimulation lead may include a lead distal end including one or more electrodes and a lead proximal end including a lead connector. The lead connector may include one or more electrode contacts electrically connected to the one or more electrodes. The stimulation lead may be configured to be percutaneously introduced into the patient to place the one or more electrodes in the patient. The sensing reference electrode may be configured to be placed in the patient. The sensing wire may include a wire distal end connected to the sensing referenced electrode and a wire proximal end including a wire connector. The wire connector may include a sensing reference electrode contact electrically connected to the sensing reference electrode. The sensing wire may be configured to be percutaneously introduced into the patient to place the sensing reference electrode in the patient. At least a portion of the sensing wire may be separated from the stimulation lead. The connection system may be configured to be placed externally to the patient, to mate the lead connector, to mate the wire connector, and to provide electrical connections between the lead connector and the test device and between the wire connector and the test device.

In Example 2, the subject matter of Example 1 may optionally be configured such that the connection system includes a cable assembly including a cable connector and a cable. The cable connector may be configured to mate the lead connector and to mate the wire connector. The cable may be configured to be connected to the cable connector and to provide electrical connections between the cable connector and the test device.

In Example 3, the subject matter of any one or a combination of Examples 1 and 2 may optionally be configured such that the stimulation lead includes an implantable lead.

In Example 4, the subject matter of any one or any combination of Examples 1 to 3 may optionally be configured such that the sensing reference electrode is attached to the stimulation lead.

In Example 5, the subject matter of Example 4 may optionally be configured such that the sensing reference electrode is detachably attached to the stimulation lead.

In Example 6, the subject matter of Example 4 may optionally be configured such that the sensing reference electrode is permanently attached the stimulation lead, and the wire distal end of the sensing wire is releasably connected to the sensing referenced electrode.

In Example 7, the subject matter of any one or any combination of Examples 1 to 3 may optionally be configured such that the sensing reference electrode is integrated into the stimulation lead.

In Example 8, the subject matter of Example 7 may optionally be configured such that at least a portion of the sensing wire is integrated into the stimulation lead.

In Example 9, the subject matter of Example 8 may optionally be configured such that the sensing wire is fully integrated into the stimulation lead, and the wire connector is integrated into the stimulation connector.

In Example 10, the subject matter of Example 8 may optionally be configured such that the sensing wire is partially integrated into the stimulation lead, and the wire connector is separate from the stimulation connector.

In Example 11, the subject matter of any one or any combination of Examples 1 to 3 may optionally be configured to further include a lead introducer including an introducer distal end configured to enter the patient, an introducer proximal end, an elongate introducer body coupled between the introducer distal end and the introducer proximal end, and a lumen extending within the introducer body from an introducer distal opening at or near the introducer distal end and an introducer proximal opening at or near the introducer proximal end. The lumen is configured to accommodate a portion of the stimulation lead and to allow the lead distal end to enter the introducer primary opening and exit from the introducer distal opening.

In Example 12, the subject matter of Example 11 may optionally be configured such that the sensing reference electrode is attached to the stimulation lead, the lumen of the lead introducer is configured to accommodate the portion of the stimulation lead, the sensing reference electrode, and a portion of the sensing wire, and the lead introducer is removable from the patient after the stimulation lead is percutaneously placed.

In Example 13, the subject matter of Example 11 may optionally be configured such that the sensing reference electrode is detachably attached to the lead introducer.

In Example 14, the subject matter of Example 13 may optionally be configured such that the lead introducer is removable from the patient after the stimulation lead is percutaneously placed, and the sensing reference electrode is configured to be detached from the lead introducer to remain in the patient after the lead introducer is removed from the patient.

In Example 15, the subject matter of Example 14 may optionally be configured to further include a releasable clip and a release handle. The releasable clip is configured to attach the sensing reference electrode to the lead introducer and to detach the sensing reference electrode from the lead introducer. The release handle is coupled to the releasable clip and configured to detach the sensing reference electrode from the introducer by releasing the releasable clip.

In Example 16, the subject matter of any one or any combination of Examples 1 to 15 may optionally be configured such that the cable is configured to be releasably connected to the cable connector.

An example (e.g., "Example 17") of a method for percutaneously delivering neurostimulation energy to a patient and sensing one or more signals from the patient using a test device placed externally to the patient is also provided. The method may include providing an elongate stimulation lead suitable for percutaneously introducing one or more electrodes into the patient for delivering the neurostimulation energy and sensing the one or more signals. The stimulation lead may include a lead distal end including the one or more electrodes and a lead proximal end including a lead connector having one or more electrode contacts electrically connected to the one or more electrodes. The method may further include providing a sensing reference electrode suitable for placing in the patient and providing an elongate sensing wire suitable for percutaneously introducing the sensing reference electrode into the patient to provide a reference for sensing the one or more signals. The sensing wire may be partially separated from the stimulation lead and may include a wire distal end connected to the sensing referenced electrode and a wire proximal end including a wire connector having a sensing reference electrode contact electrically connected to the sensing reference electrode. The method may still include providing electrical connections external to the patient for connecting the test device to the lead connector and to the wire connector.

In Example 18, the subject matter of providing the electrical connections between the lead connector and the test device and between the wire connector and the test device as found in Example 17 may optionally include providing a cable assembly for connecting the test device to the stimulation lead and to the sensing wire. The cable assembly may include a cable connector configured to mate the lead connector and to mate the wire connector and a cable connected to the cable connector and providing electrical connections between the cable connector and the test device.

In Example 19, the subject matter of providing the elongate stimulation lead as found in any one or a combination of Examples 17 and 18 may optionally include providing an implantable lead.

In Example 20, the subject matter of any one or any combination of Examples 17 to 19 may optionally further include attaching sensing reference electrode to the stimulation lead.

In Example 21, the subject matter of any one or any combination of Examples 17 to 19 may optionally further include integrating the sensing reference electrode into the stimulation lead.

In Example 22, the subject matter of any one or any combination of Examples 17 to 19 may optionally further include providing a lead introducer suitable for percutaneously introducing the stimulation lead for placing the one or more electrode in the patient. The lead introducer includes an introducer distal end configured to enter the patient, an introducer proximal end, an elongate introducer body coupled between the introducer distal end and the introducer proximal end, and a lumen extending within the introducer body from an introducer distal opening at or near the introducer distal end and an introducer proximal opening at or near the introducer proximal end. The lumen is configured to accommodate a portion of the stimulation lead and to allow the lead distal end to enter the introducer primary opening and exit from the introducer distal opening.

In Example 23, the subject matter of Example 22 may optionally further include detachably attach the sensing reference electrode to the lead introducer.

In Example 24, the subject matter of Example 23 may optionally further include detaching the sensing reference electrode from the lead introducer after the stimulation lead is percutaneously introduced using the lead introducer.

In Example 25, the subject matter of Example 24 may optionally further include providing a releasable clip to attach the sensing reference electrode to the lead introducer and a release handle coupled to the releasable clip, and the subject matter of detaching the sensing reference electrode from the lead introducer as found in Example 22 may optionally include releasing the releasable clip using the release handle.

In Example 26, the subject matter of any one or any combination of Examples 17 to 25 may optionally further include percutaneously introducing the stimulation lead to place the one or more electrodes subcutaneously over the spinal cord of the patient, sensing the one or more signals using the one or more electrodes placed subcutaneously over the spinal cord, and processing the sensed one or more signals using the test device.

In Example 27, the subject matter of Example 26 may optionally further include generating the neurostimulation energy using the test device and delivering the neurostimulation energy to the spinal cord using the one or more electrodes.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense.

The scope of the present disclosure is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

Figure 1:
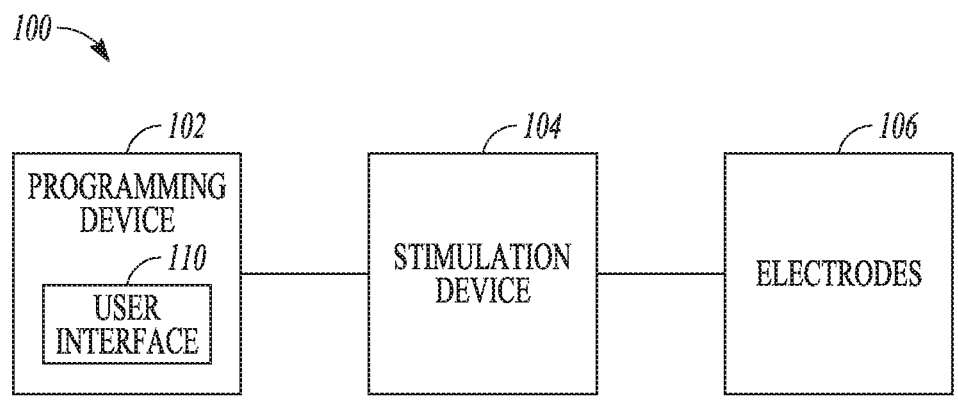
FIG. 1 illustrates an embodiment of a neurostimulation system.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized, and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

This document discusses, among other things, an external trial neurostimulation system with sensing and stimulation capabilities. In various embodiments, the external trial neurostimulation system can be used to evaluate a patient for potentially receiving a neuromodulation system that includes an implantable device configured to deliver a neurostimulation (also referred to as neuromodulation) therapy. Examples of such a neurostimulation therapy include, but are not limited to, deep brain stimulation (DBS), spinal cord stimulation (SCS), peripheral nerve stimulation (PNS), and vagus nerve stimulation (VNS). In this document, a "patient" includes a person receiving treatment delivered using a neurostimulation system according to the present subject matter, and a "user" includes a physician or other caregiver who treats the patient using the neurostimulation system.

The external trial neurostimulation system can use external equipment (that is to be placed externally to the patient's body) connected with percutaneous or implantable leads having electrodes placed inside the patient's body to assess potential effectiveness of a neurostimulation therapy. While SCS is discussed and illustrated as a specific example, the present subject matter can apply to any neurostimulation therapy for which the patient can benefit from the assessment of potential effectiveness using the external equipment. The external equipment can include biopotential sensing functions. Such biopotential sensing functions can include, for example, sensing functions that are available from an implantable device that delivers the neurostimulation therapy to be evaluated, such as an implantable neurostimulator including nerve signal sensing capability. It can be desirable to use the external trial neurostimulation system to emulate the sensing functions of the implantable device.

To sense signals arising within the patient's body using the external equipment, a reference voltage obtained from the patient's body is frequently used in the art to reduce common mode noise voltage differences between the patient's body and the external equipment. An external sensing reference electrode can be attached to the patient's skin to provide the reference voltage. However, if the external equipment is to remain connected to the patient for an extended period of time, e.g., hours or days, it can be advantageous to place an implantable electrode inside the patient's body for providing the reference voltage. This prevents the patient from wearing an external electrode on the skin for an extended period of time, which can be inconvenient to the patient while resulting in a poor referencing connection over the duration of the assessment that can last for hours to days with the patient carrying the external equipment during daily activities. An implantable lead or a percutaneous lead that can emulate the implantable lead with electrodes placed in the actual sensing and stimulation sites can be used such that the sensing and stimulation functions of the implantable device in the actual environment can be accurately evaluated.

FIG. 1 illustrates an embodiment of a neurostimulation system 100. System 100 includes electrodes 106, a stimulation device 104, and a programming device 102. Electrodes 106 are configured to be placed on or near one or more neural targets in a patient. Stimulation device 104 is configured to be electrically connected to electrodes 106 and deliver neurostimulation energy, such as in the form of electrical pulses, to the one or more neural targets though electrodes 106. The delivery of the neurostimulation is controlled by using a plurality of stimulation parameters, such as stimulation parameters specifying a pattern of the electrical pulses and a selection of electrodes through which each of the electrical pulses is delivered. In various embodiments, at least some parameters of the plurality of stimulation parameters are programmable by a user, such as a physician or other caregiver who treats the patient using system 100. Programming device 102 provides the user with accessibility to the user-programmable parameters. In various embodiments, programming device 102 is configured to be communicatively coupled to stimulation device via a wired or wireless link.

In this document, a "user" includes a physician or other clinician or caregiver who treats the patient using system 100; a "patient" includes a person who receives or is intended to receive neurostimulation delivered using system 100. In various embodiments, the patient can be allowed to adjust his or her treatment using system 100 to certain extent, such as by adjusting certain therapy parameters and entering feedback and clinical effect information.

In various embodiments, programming device 102 can include a user interface 110 that allows the user to control the operation of system 100 and monitor the performance of system 100 as well as conditions of the patient including responses to the delivery of the neurostimulation. The user can control the operation of system 100 by setting and/or adjusting values of the user-programmable parameters.

In various embodiments, user interface 110 can include a graphical user interface (GUI) that allows the user to set and/or adjust the values of the user-programmable parameters by creating and/or editing graphical representations of various waveforms. Such waveforms can include, for example, a waveform representing a pattern of neurostimulation pulses to be delivered to the patient as well as individual waveforms that are used as building blocks of the pattern of neurostimulation pulses, such as the waveform of each pulse in the pattern of neurostimulation pulses. The GUI can also allow the user to set and/or adjust stimulation fields each defined by a set of electrodes through which one or more neurostimulation pulses represented by a waveform are delivered to the patient. The stimulation fields can each be further defined by the distribution of the current of each neurostimulation pulse in the waveform. In various embodiments, neurostimulation pulses for a stimulation period (such as the duration of a therapy session) can be delivered to multiple stimulation fields.

In various embodiments, system 100 can be configured for neurostimulation applications. User interface 110 can be configured to allow the user to control the operation of system 100 for neurostimulation. For example, system 100 as well as user interface 100 can be configured for DBS applications. Such DBS configuration includes various features that can simplify the task of the user in programming stimulation device 104 for delivering DBS to the patient, such as the features discussed in this document.

Figure 2:
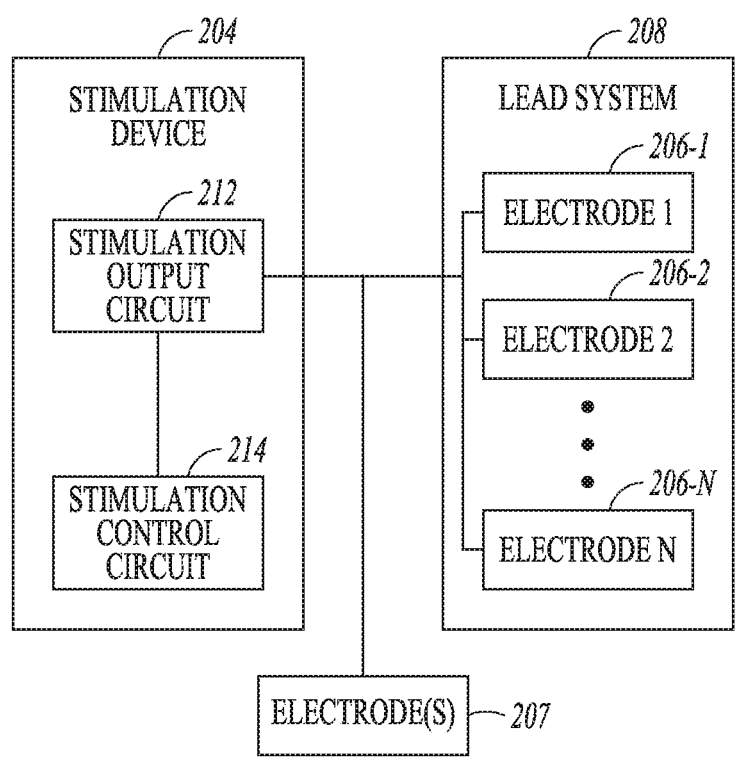
FIG. 2 illustrates an embodiment of a stimulation device and a lead system, such as may be implemented in the neurostimulation system of FIG. 1.

FIG. 2 illustrates an embodiment of a stimulation device 204 and a lead system 208, such as may be implemented in neurostimulation system 100.

Stimulation device 204 represents an example of stimulation device 104 and includes a stimulation output circuit 212 and a stimulation control circuit 214. Stimulation output circuit 212 produces and delivers neurostimulation pulses. Stimulation control circuit 214 controls the delivery of the neurostimulation pulses from stimulation output circuit 212 using the plurality of stimulation parameters, which specifies a pattern of the neurostimulation pulses. Lead system 208 includes one or more leads each configured to be electrically connected to stimulation device 204 and a plurality of electrodes 206 distributed in the one or more leads. The plurality of electrodes 206 includes electrode 206-1, electrode 206-2, . . . electrode 206-N, each a single electrically conductive contact providing for an electrical interface between stimulation output circuit 212 and tissue of the patient, where N≥2. The neurostimulation pulses are each delivered from stimulation output circuit 212 through a set of electrodes selected from electrodes 206. In various embodiments, the neurostimulation pulses can include one or more individually defined pulses, and the set of electrodes can be individually definable by the user for each of the individually defined pulses or each of collections of pulse intended to be delivered using the same combination of electrodes. In various embodiments, one or more additional electrodes 207 (each of which may be referred to as a reference electrode) can be electrically connected to stimulation device 204, such as one or more electrodes each being a portion of or otherwise incorporated onto a housing of stimulation device 204. Monopolar stimulation uses a monopolar electrode configuration with one or more electrodes selected from electrodes 206 and at least one electrode from electrode(s) 207. Bipolar stimulation uses a bipolar electrode configuration with two electrodes selected from electrodes 206 and none electrode(s) 207. Multipolar stimulation uses a multipolar electrode configuration with multiple (two or more) electrodes selected from electrodes 206 and none of electrode(s) 207.

In various embodiments, the number of leads and the number of electrodes on each lead depend on, for example, the distribution of target(s) of the neurostimulation and the need for controlling the distribution of electric field at each target. In one embodiment, lead system 208 includes 2 leads each having 8 electrodes.

Figure 3:
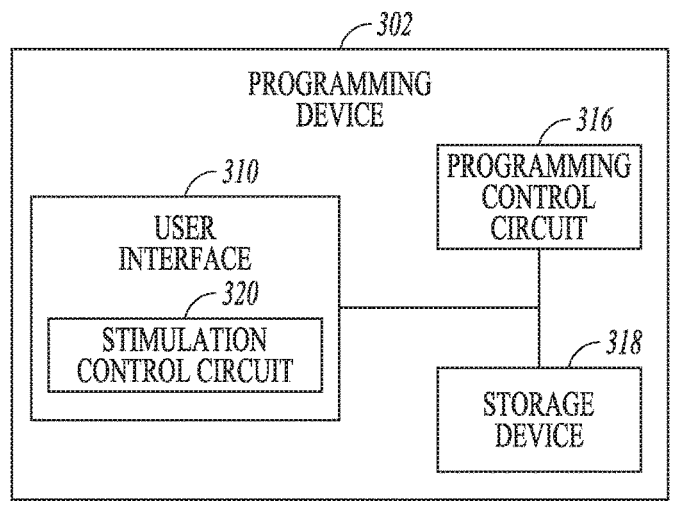
FIG. 3 illustrates an embodiment of a programming device, such as may be implemented in the neurostimulation system of FIG. 1.

FIG. 3 illustrates an embodiment of a programming device 302, such as may be implemented in neurostimulation system 100. Programming device 302 represents an example of programming device 102 and includes a storage device 318, a programming control circuit 316, and a user interface 310. Programming control circuit 316 generates the plurality of stimulation parameters that controls the delivery of the neurostimulation pulses according to a specified neurostimulation program that can define, for example, stimulation waveform and electrode configuration. User interface 310 represents an example of user interface 110 and includes a stimulation control circuit 320. Storage device 318 stores information used by programming control circuit 316 and stimulation control circuit 320, such as information about a stimulation device that relates the neurostimulation program to the plurality of stimulation parameters. In various embodiments, stimulation control circuit 320 can be configured to support one or more functions allowing for programming of stimulation devices, such as stimulation device 104 including its various embodiments as discussed in this document, according to one or more selected neurostimulation programs as discussed in this document.

In various embodiments, user interface 310 can allow for definition of a pattern of neurostimulation pulses for delivery during a neurostimulation therapy session by creating and/or adjusting one or more stimulation waveforms using a graphical method. The definition can also include definition of one or more stimulation fields each associated with one or more pulses in the pattern of neurostimulation pulses. As used in this document, a "neurostimulation program" can include the pattern of neurostimulation pulses including the one or more stimulation fields, or at least various aspects or parameters of the pattern of neurostimulation pulses including the one or more stimulation fields. In various embodiments, user interface 310 includes a GUI that allows the user to define the pattern of neurostimulation pulses and perform other functions using graphical methods. In this document, "neurostimulation programming" can include the definition of the one or more stimulation waveforms, including the definition of one or more stimulation fields.

In various embodiments, circuits of neurostimulation 100, including its various embodiments discussed in this document, may be implemented using a combination of hardware and software. For example, the circuit of user interface 110, stimulation control circuit 214, programming control circuit 316, and stimulation control circuit 320, including their various embodiments discussed in this document, may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 4:
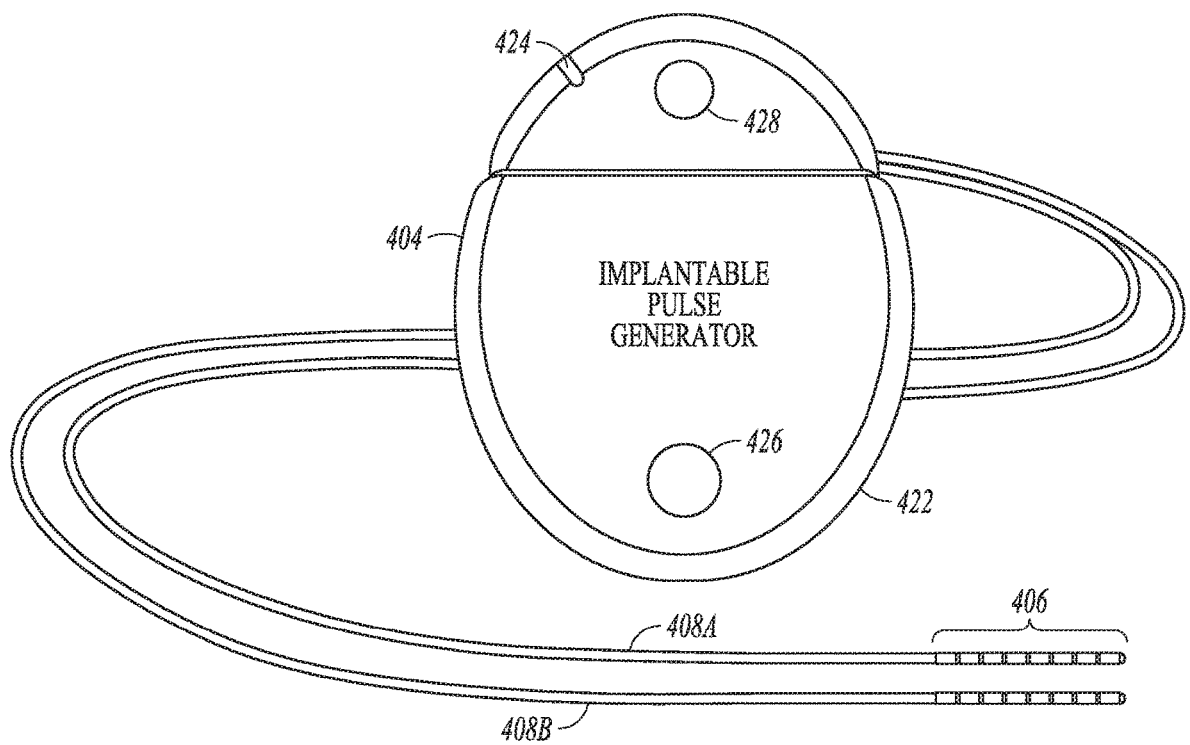
FIG. 4 illustrates an embodiment of an implantable pulse generator (IPG) and an implantable lead system, such as an example implementation of the stimulation device and lead system of FIG. 2.

FIG. 4 illustrates an embodiment of an implantable pulse generator (IPG) 404 and an implantable lead system 408. IPG 404 represents an example implementation of stimulation device 204. Lead system 408 represents an example implementation of lead system 208. As illustrated in FIG. 4, IPG 404 that can be coupled to implantable leads 408A and 408B at a proximal end of each lead. The distal end of each lead includes electrical contacts or electrodes 406 for contacting a tissue site targeted for electrical neurostimulation. As illustrated in FIG. 1, leads 408A and 408B each include 8 electrodes 406 at the distal end. The number and arrangement of leads 408A and 408B and electrodes 406 as shown in FIG. 1 are only an example, and other numbers and arrangements are possible. In various embodiments, the electrodes are ring electrodes. The implantable leads and electrodes can be configured by shape and size to provide electrical neurostimulation energy to a neuronal target included in the subject's brain or configured to provide electrical neurostimulation energy to a nerve cell target included in the subject's spinal cord.

Figure 5:
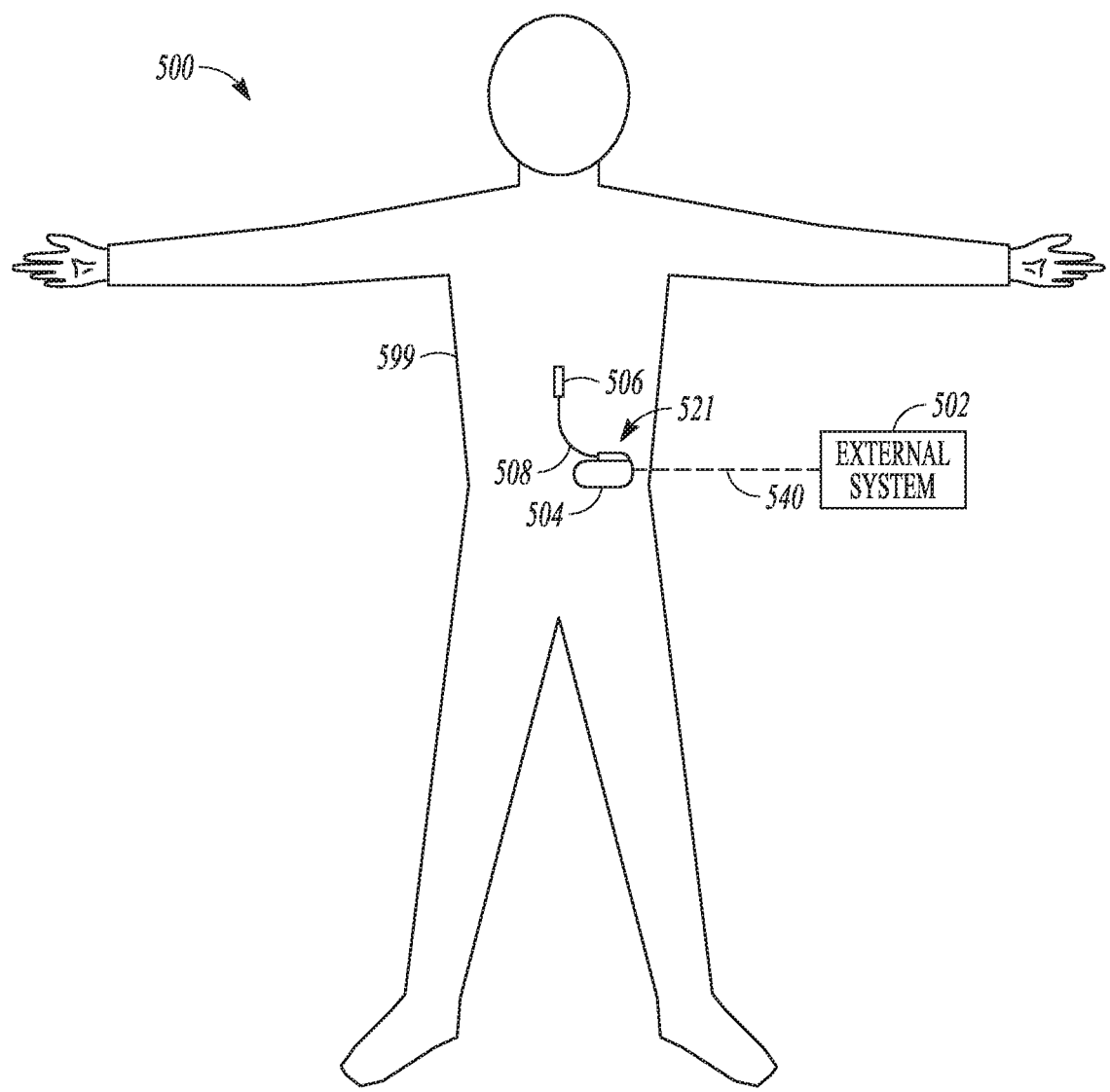
FIG. 5 illustrates an embodiment of an IPG and an implantable lead system, such as the IPG and lead system of FIG. 4, arranged to provide neurostimulation to a patient.

FIG. 5 illustrates an implantable neurostimulation system 500 and portions of an environment in which system 500 can be used. System 500 includes an implantable system 521, an external system 502, and a telemetry link 540 providing for wireless communication between implantable system 521 and external system 502. Implantable system 521 is illustrated in FIG. 5 as being implanted in the patient's body 599.

Implantable system 521 includes an implantable stimulator (also referred to as an implantable pulse generator, or IPG) 504, a lead system 508, and electrodes 506, which represent an example of stimulation device 204, lead system 208, and electrodes 206, respectively. External system 502 represents an example of programming device 302. In various embodiments, external system 502 includes one or more external (non-implantable) devices each allowing the user and/or the patient to communicate with implantable system 521. In some embodiments, external 502 includes a programming device intended for the user to initialize and adjust settings for implantable stimulator 504 and a remote control device intended for use by the patient. For example, the remote control device can allow the patient to turn implantable stimulator 504 on and off and/or adjust certain patient-programmable parameters of the plurality of stimulation parameters.

The sizes and sharps of the elements of implantable system 521 and their location in body 599 are illustrated by way of example and not by way of restriction. An implantable system is discussed as a specific application of the programming according to various embodiments of the present subject matter. In various embodiments, the present subject matter can be applied in programming any type of stimulation device that uses electrical pulses as stimuli, regarding less of stimulation targets in the patient's body and whether the stimulation device is implantable.

Returning to FIG. 4, the IPG 404 can include a hermetically-sealed IPG case 422 to house the electronic circuitry of IPG 404. IPG 404 can include an electrode 426 formed on IPG case 422. IPG 404 can include an IPG header 424 for coupling the proximal ends of leads 408A and 408B. IPG header 424 can optionally also include an electrode 428. Electrodes 426 and/or 428 represent embodiments of electrode(s) 207 and can each be referred to as a reference electrode.

Neurostimulation energy can be delivered in a monopolar (also referred to as unipolar) mode using electrode 426 or electrode 428 and one or more electrodes selected from electrodes 406. Neurostimulation energy can be delivered in a bipolar mode using a pair of electrodes of the same lead (lead 408A or lead 408B). Neurostimulation energy can be delivered in an extended bipolar mode using one or more electrodes of a lead (e.g., one or more electrodes of lead 408A) and one or more electrodes of a different lead (e.g., one or more electrodes of lead 408B).

The electronic circuitry of IPG 404 can include a control circuit that controls delivery of the neurostimulation energy. The control circuit can include a microprocessor, a digital signal processor, application specific integrated circuit (ASIC), or other type of processor, interpreting or executing instructions included in software or firmware. The neurostimulation energy can be delivered according to specified (e.g., programmed) modulation parameters. Examples of setting modulation parameters can include, among other things, selecting the electrodes or electrode combinations used in the stimulation, configuring an electrode or electrodes as the anode or the cathode for the stimulation, specifying the percentage of the neurostimulation provided by an electrode or electrode combination, and specifying stimulation pulse parameters. Examples of pulse parameters include, among other things, the amplitude of a pulse (specified in current or voltage), pulse duration (e.g., in microseconds), pulse rate (e.g., in pulses per second), and parameters associated with a pulse train or pattern such as burst rate (e.g., an "on" modulation time followed by an "off" modulation time), amplitudes of pulses in the pulse train, polarity of the pulses, etc.

Figure 6:
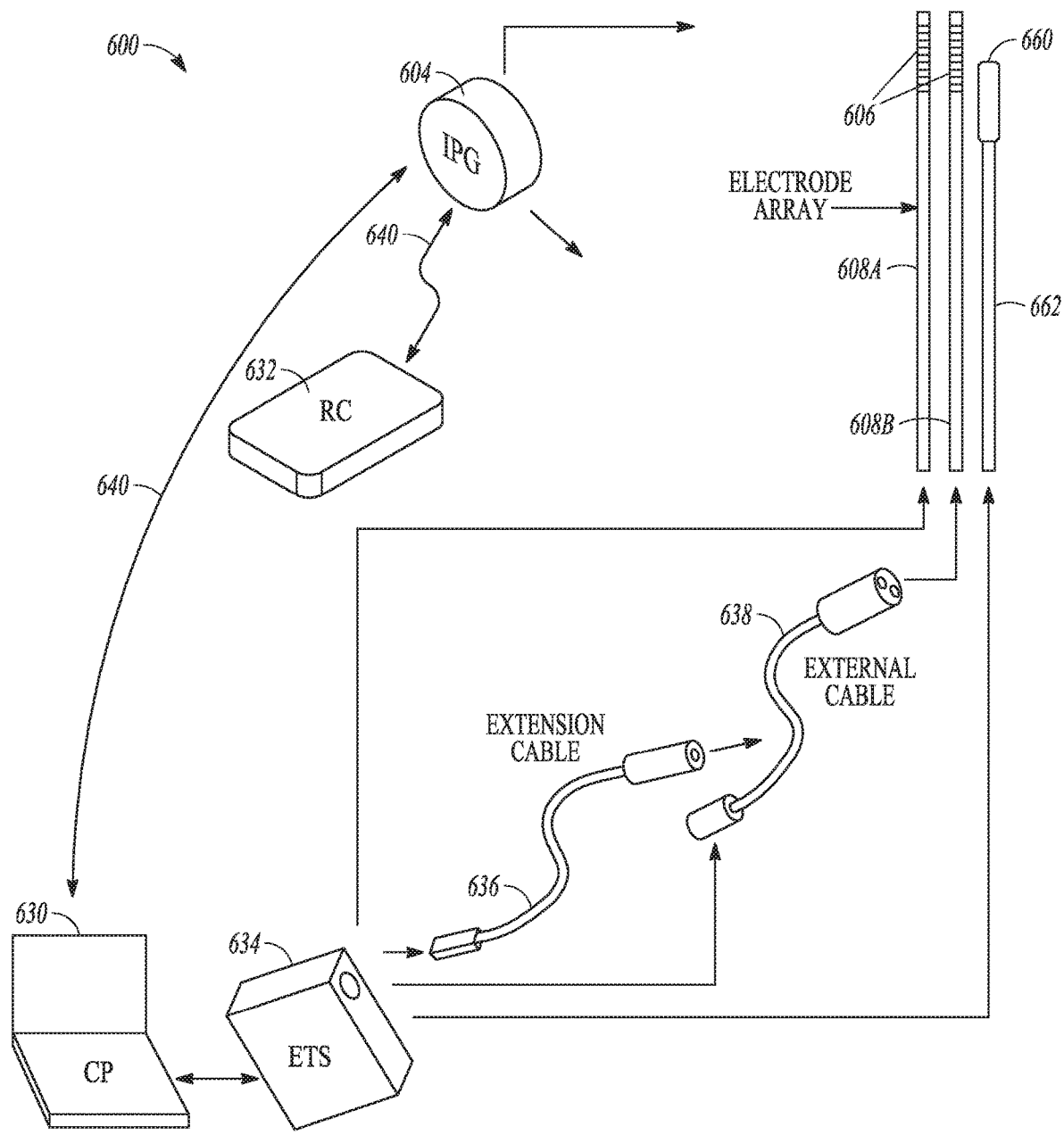
FIG. 6 illustrates an embodiment of portions of a neurostimulation system.

FIG. 6 illustrates an embodiment of portions of a neurostimulation system 600. System 600 includes an IPG 604, implantable neurostimulation leads 608A and 608B, an external remote controller (RC) 632, a clinician's programmer (CP) 630, and an external trial stimulator (ETS, also referred to as external trial modulator, or ETM) 634. IPG 404 can be electrically coupled to leads 608A and 608B directly. In various embodiments in which ETS 634 includes sensing capabilities, a sensing reference electrode 660 connected to a sensing wire 662 is provided. ETS 634 can be electrically connected to each of leads 608A and 608B and sensing wire 662 directly or via extension cable 636 and/or external cable 638. Various embodiments of sensing reference electrode 660 with sensing wire 662 are discussed below, with reference to FIGS. 9-13.

System 600 represents an example of system 100, with IPG 604 representing an embodiment of stimulation device 104, electrodes 606 of leads 608A and 608B representing electrodes 106, and CP 630, RC 632, and ETS 634 collectively representing programming device 102.

ETS 634 can be standalone or incorporated into CP 630. ETS 634 can have similar pulse generation circuitry as IPG 604 to deliver neurostimulation energy according to specified modulation parameters as discussed above. ETS 634 is an external device that is typically used as a preliminary stimulator after leads 408A and 408B have been implanted and used prior to stimulation with IPG 604 to test the patient's responsiveness to the stimulation that is to be provided by IPG 604. Because ETS 634 is external it can be more easily configurable than IPG 604.

CP 630 can configure the neurostimulation provided by ETS 634. If ETS 634 is not integrated into CP 630, CP 630 can communicate with ETS 634 using a wired connection (e.g., over a USB link) or by wireless telemetry using a wireless communications link 640. CP 630 also communicates with IPG 604 using a wireless communications link 640.

An example of wireless telemetry is based on inductive coupling between two closely-placed coils using the mutual inductance between these coils. This type of telemetry is referred to as inductive telemetry or near-field telemetry because the coils must typically be closely situated for obtaining inductively coupled communication. IPG 604 can include the first coil and a communication circuit. CP 630 can include or otherwise electrically connected to the second coil such as in the form of a wand that can be place near IPG 604. Another example of wireless telemetry includes a far-field telemetry link, also referred to as a radio frequency (RF) telemetry link. A far-field, also referred to as the Fraunhofer zone, refers to the zone in which a component of an electromagnetic field produced by the transmitting electromagnetic radiation source decays substantially proportionally to 1/r, where r is the distance between an observation point and the radiation source. Accordingly, far-field refers to the zone outside the boundary of $r=\lambda/2\pi$, where $\lambda$ is the wavelength of the transmitted electromagnetic energy. In one example, a communication range of an RF telemetry link is at least six feet but can be as long as allowed by the particular communication technology. RF antennas can be included, for example, in the header of IPG 604 and in the housing of CP 630, eliminating the need for a wand or other means of inductive coupling. An example is such an RF telemetry link is a Bluetooth® wireless link.

CP 630 can be used to set modulation parameters for the neurostimulation after IPG 604 has been implanted. This allows the neurostimulation to be tuned if the requirements for the neurostimulation change after implantation. CP 630 can also upload information from IPG 604.

RC 632 also communicates with IPG 604 using a wireless link 340. RC 632 can be a communication device used by the user or given to the patient. RC 632 can have reduced programming capability compared to CP 630. This allows the user or patient to alter the neurostimulation therapy but does not allow the patient full control over the therapy. For example, the patient may be able to increase the amplitude of neurostimulation pulses or change the time that a pre-programmed stimulation pulse train is applied. RC 632 can be programmed by CP 630. CP 630 can communicate with the RC 632 using a wired or wireless communications link.

In some embodiments, CP 630 can program RC 632 when remotely located from RC 632.

Figure 7:
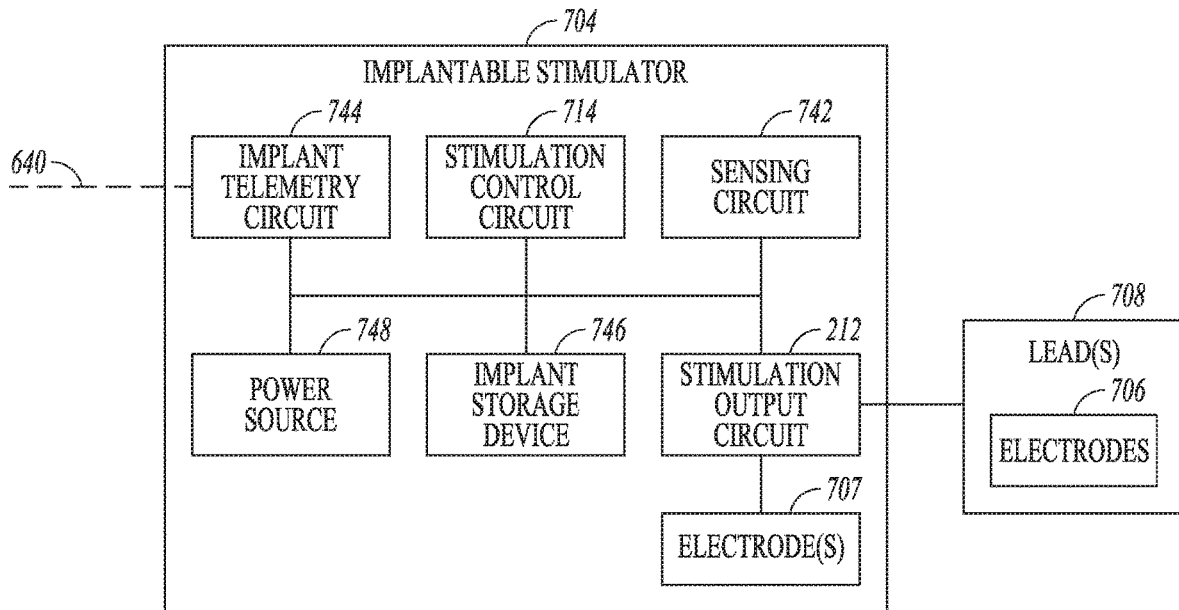
FIG. 7 illustrates an embodiment of an implantable stimulator and one or more leads of an implantable neurostimulation system, such as the implantable neurostimulation system of FIG. 6.

FIG. 7 illustrates an embodiment of implantable stimulator 704 and one or more leads 708 of an implantable neurostimulation system, such as implantable system 600. Implantable stimulator 704 represents an example of stimulation device 104 or 204 and can be implemented, for example, as IPG 604. Lead(s) 708 represents an example of lead system 208 and can be implemented, for example, as implantable leads 608A and 608B. Lead(s) 708 includes electrodes 706, which represents an example of electrodes 106 or 206 and can be implemented as electrodes 606.

Implantable stimulator 704 can include a sensing circuit 742 that is optional and required when the stimulator needs a sensing capability, stimulation output circuit 212, a stimulation control circuit 714, an implant storage device 746, an implant telemetry circuit 744, a power source 748, and one or more electrodes 707. Sensing circuit 742, when included and needed, senses one or more physiological signals for purposes of patient monitoring and/or feedback control of the neurostimulation. Examples of the one or more physiological signals include neural and other biopotential signals each indicative of a condition of the patient that is treated by the neurostimulation and/or a response of the patient to the delivery of the neurostimulation. Stimulation output circuit 212 is electrically connected to electrodes 706 through one or more leads 708 as well as electrodes 707 and delivers each of the neurostimulation pulses through a set of electrodes selected from electrodes 706 and electrode(s) 707. Stimulation control circuit 714 represents an example of stimulation control circuit 214 and controls the delivery of the neurostimulation pulses using the plurality of stimulation parameters specifying the pattern of neurostimulation pulses. In one embodiment, stimulation control circuit 714 controls the delivery of the neurostimulation pulses using the one or more sensed physiological signals. Implant telemetry circuit 744 provides implantable stimulator 704 with wireless communication with another device such as CP 630 and RC 632, including receiving values of the plurality of stimulation parameters from the other device. Implant storage device 746 can store one or more neurostimulation programs and values of the plurality of stimulation parameters for each of the one or more neurostimulation programs. Power source 748 provides implantable stimulator 704 with energy for its operation. In one embodiment, power source 748 includes a battery. In one embodiment, power source 748 includes a rechargeable battery and a battery charging circuit for charging the rechargeable battery. Implant telemetry circuit 744 can also function as a power receiver that receives power transmitted from an external device through an inductive couple. Electrode(s) 707 allow for delivery of the neurostimulation pulses in the monopolar mode. Examples of electrode(s) 707 include electrode 426 and electrode 418 in IPG 404 as illustrated in FIG. 4.

In one embodiment, implantable stimulator 704 is used as a master database. A patient implanted with implantable stimulator 704 (such as may be implemented as IPG 604) can therefore carry patient information needed for his or her medical care when such information is otherwise unavailable. Implant storage device 746 is configured to store such patient information. For example, the patient can be given a new RC 632 and/or travel to a new clinic where a new CP 630 is used to communicate with the device implanted in him or her. The new RC 632 and/or CP 630 can communicate with implantable stimulator 704 to retrieve the patient information stored in implant storage device 746 through implant telemetry circuit 744 and wireless communication link 640 and allow for any necessary adjustment of the operation of implantable stimulator 704 based on the retrieved patient information. In various embodiments, the patient information to be stored in implant storage device 746 can include, for example, positions of lead(s) 708 and electrodes 706 relative to the patient's anatomy (transformation for fusing computerized tomogram (CT) of post-operative lead placement to magnetic resonance imaging (MRI) of the brain), clinical effect map data, objective measurements using quantitative assessments of symptoms (for example using micro-electrode recording, accelerometers, and/or other sensors), and/or any other information considered important or useful for providing adequate care for the patient. In various embodiments, the patient information to be stored in implant storage device 746 can include data transmitted to implantable stimulator 704 for storage as part of the patient information and data acquired by implantable stimulator 704, such as by using sensing circuit 742.

In various embodiments, sensing circuit 742 (if included), stimulation output circuit 212, stimulation control circuit 714, implant telemetry circuit 744, implant storage device 746, and power source 748 are encapsulated in a hermetically sealed implantable housing or case, and electrode(s) 707 are formed or otherwise incorporated onto the case. In various embodiments, lead(s) 708 are implanted such that electrodes 706 are placed on and/or around one or more targets to which the neurostimulation pulses are to be delivered, while implantable stimulator 704 is subcutaneously implanted and connected to lead(s) 708 at the time of implantation.

Figure 8:
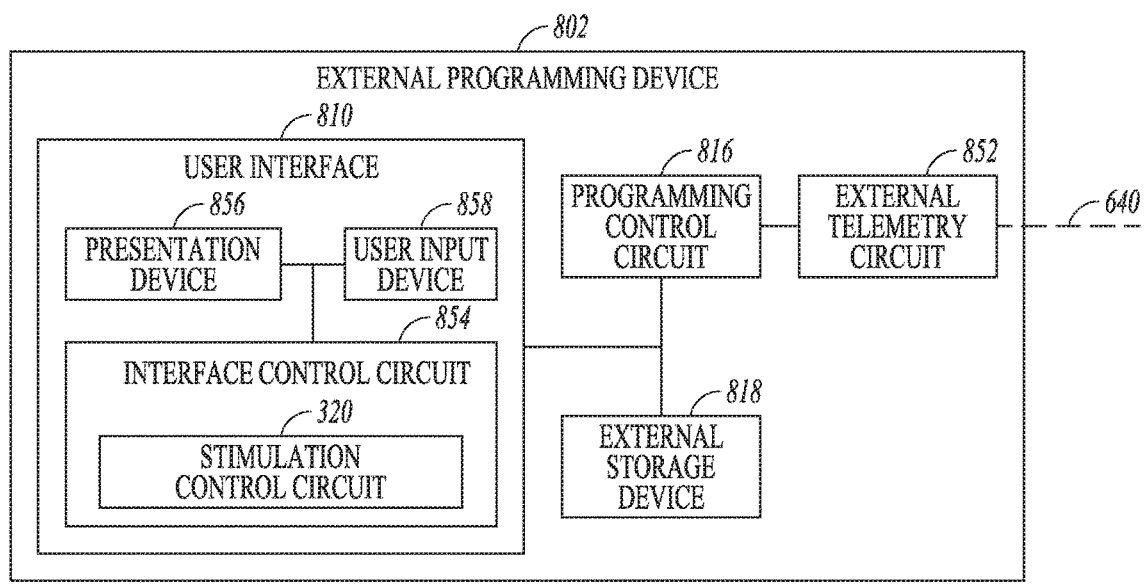
FIG. 8 illustrates an embodiment of an external programming device of an implantable neurostimulation system, such as the implantable neurostimulation system of FIG. 6.

FIG. 8 illustrates an embodiment of an external programming device 802 of an implantable neurostimulation system, such as system 600. External programming device 802 represents an example of programming device 102 or 302, and can be implemented, for example, as CP 630 and/or RC 632. External programming device 802 includes an external telemetry circuit 852, an external storage device 818, a programming control circuit 816, and a user interface 810.

External telemetry circuit 852 provides external programming device 802 with wireless communication with another device such as implantable stimulator 704 via wireless communication link 640, including transmitting the plurality of stimulation parameters to implantable stimulator 704 and receiving information including the patient data from implantable stimulator 704. In one embodiment, external telemetry circuit 852 also transmits power to implantable stimulator 704 through an inductive couple.

In various embodiments, wireless communication link 640 can include an inductive telemetry link (near-field telemetry link) and/or a far-field telemetry link (RF telemetry link). For example, because DBS is often indicated for movement disorders which are assessed through patient activities, gait, balance, etc., allowing patient mobility during programming and assessment is useful. Therefore, when system 600 is intended for applications including DBS, wireless communication link 640 includes at least a far-field telemetry link that allows for communications between external programming device 802 and implantable stimulator 704 over a relative long distance, such as up to about 20 meters. External telemetry circuit 852 and implant telemetry circuit 744 each include an antenna and RF circuitry configured to support such wireless telemetry.

External storage device 818 stores one or more stimulation waveforms for delivery during a neurostimulation therapy session, such as a DBS therapy session, as well as various parameters and building blocks for defining one or more waveforms. The one or more stimulation waveforms can each be associated with one or more stimulation fields and represent a pattern of neurostimulation pulses to be delivered to the one or more stimulation field during the neurostimulation therapy session. In various embodiments, each of the one or more stimulation waveforms can be selected for modification by the user and/or for use in programming a stimulation device such as implantable stimulator 704 to deliver a therapy. In various embodiments, each waveform in the one or more stimulation waveforms is definable on a pulse-by-pulse basis, and external storage device 818 can include a pulse library that stores one or more individually definable pulse waveforms each defining a pulse type of one or more pulse types. External storage device 818 also stores one or more individually definable stimulation fields. Each waveform in the one or more stimulation waveforms is associated with at least one field of the one or more individually definable stimulation fields. Each field of the one or more individually definable stimulation fields is defined by a set of electrodes through a neurostimulation pulse is delivered. In various embodiments, each field of the one or more individually definable fields is defined by the set of electrodes through which the neurostimulation pulse is delivered and a current distribution of the neurostimulation pulse over the set of electrodes. In one embodiment, the current distribution is defined by assigning a fraction of an overall pulse amplitude to each electrode of the set of electrodes. Such definition of the current distribution may be referred to as "fractionalization" in this document. In another embodiment, the current distribution is defined by assigning an amplitude value to each electrode of the set of electrodes. For example, the set of electrodes can include 2 electrodes used as the anode and an electrode as the cathode for delivering a neurostimulation pulse having a pulse amplitude of 4 mA. The current distribution over the 2 electrodes used as the anode needs to be defined. In one embodiment, a percentage of the pulse amplitude is assigned to each of the 2 electrodes, such as 75% assigned to electrode 1 and 25% to electrode 2. In another embodiment, an amplitude value is assigned to each of the 2 electrodes, such as 3 mA assigned to electrode 1 and 1 mA to electrode 2. Control of the current in terms of percentages allows precise and consistent distribution of the current between electrodes even as the pulse amplitude is adjusted. It is suited for thinking about the problem as steering a stimulation locus, and stimulation changes on multiple contacts simultaneously to move the locus while holding the stimulation amount constant. Control and displaying the total current through each electrode in terms of absolute values (e.g. mA) allows precise dosing of current through each specific electrode. It is suited for changing the current one contact at a time (and allows the user to do so) to shape the stimulation like a piece of clay (pushing/pulling one spot at a time).

Programming control circuit 816 represents an example of programming control circuit 316 and generates the plurality of stimulation parameters, which is to be transmitted to implantable stimulator 704, based on a specified neurostimulation program (e.g., the pattern of neurostimulation pulses as represented by one or more stimulation waveforms and one or more stimulation fields, or at least certain aspects of the pattern). The neurostimulation program can be created and/or adjusted by the user using user interface 810 and stored in external storage device 818. In various embodiments, programming control circuit 816 can check values of the plurality of stimulation parameters against safety rules to limit these values within constraints of the safety rules. In one embodiment, the safety rules are heuristic rules.

User interface 810 represents an example of user interface 310 and allows the user to define the pattern of neurostimulation pulses and perform various other monitoring and programming tasks. User interface 810 includes a display screen 856, a user input device 858, and an interface control circuit 854. Display screen 856 can include any type of interactive or non-interactive screens, and user input device 858 can include any type of user input devices that supports the various functions discussed in this document, such as touchscreen, keyboard, keypad, touchpad, trackball, joystick, and mouse. In one embodiment, user interface 810 includes a GUI. The GUI can also allow the user to perform any functions discussed in this document where graphical presentation and/or editing are suitable as can be appreciated by those skilled in the art.

Interface control circuit 854 controls the operation of user interface 810 including responding to various inputs received by user input device 858 and defining the one or more stimulation waveforms. Interface control circuit 854 includes stimulation control circuit 320.

In various embodiments, external programming device 802 can have operation modes including a composition mode and a real-time programming mode. Under the composition mode (also known as the pulse pattern composition mode), user interface 810 is activated, while programming control circuit 816 is inactivated. Programming control circuit 816 does not dynamically updates values of the plurality of stimulation parameters in response to any change in the one or more stimulation waveforms. Under the real-time programming mode, both user interface 810 and programming control circuit 816 are activated. Programming control circuit 816 dynamically updates values of the plurality of stimulation parameters in response to changes in the set of one or more stimulation waveforms and transmits the plurality of stimulation parameters with the updated values to implantable stimulator 704.

Figure 9:
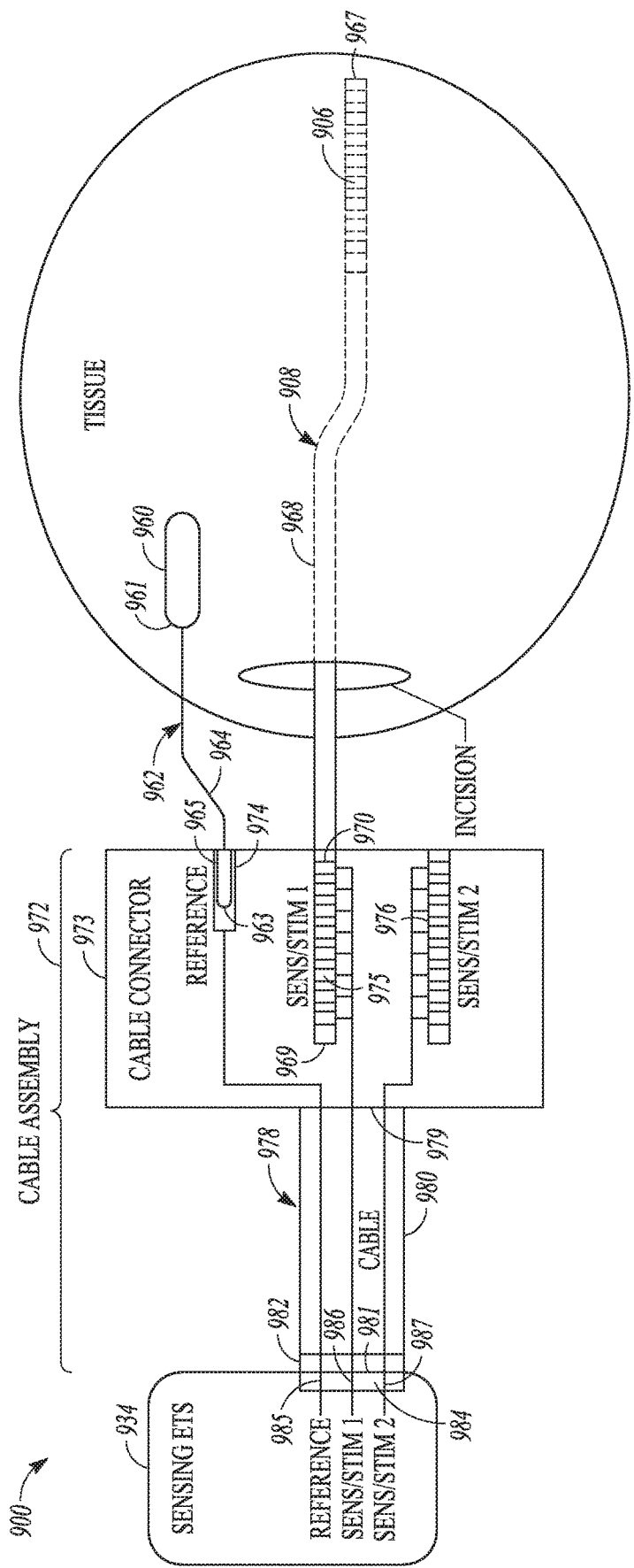
FIG. 9 illustrates an embodiment of portions of a neurostimulation trial system with an external sensing reference electrode.

FIG. 9 illustrates an embodiment of portions of a neurostimulation trial system 900. System 900 allows for percutaneously delivering neurostimulation energy to a patient and sensing one or more signal from the patient using externally equipment during a neurostimulation trial. System 900 can be used in a neurostimulation trial to emulate functions of an implantable system such as implantable system 521 for evaluate effectiveness of the functions in treating the patient. Purposes of the neurostimulation trial can include, for example, determining whether the patient should be treated using the implantable system and/or setting parameters for the treatment. In the illustrated embodiment, system 900 includes a stimulation lead 908, a sensing reference electrode 960 connected to a sensing wire 962, a sensing ETS (i.e., an ETS with sensing capabilities) 934, and a cable assembly 972. The illustrated "TISSUE" represents portions of the body tissue of the patient including where the neurostimulation energy is delivered to and the one or more signals are sensing from and where an incision is made for inserting portions of system 900 into the patient.

Stimulation lead 908 has a lead distal end 967, a lead proximal end 969, and an elongate lead body 968 coupled between lead distal end 967 and lead proximal end 969. In this document, "distal" and "proximal" are relative to sensing ETS 934 when the components of system 900 are connected as illustrated in FIGS. 9-13. Lead distal end 967 includes one or more electrodes 906 each useable for delivering the neurostimulation energy and/or sensing a signal. Lead proximal end 969 includes a lead connector 970. Lead connector 970 includes one or more electrode contacts electrically connected to one or more electrodes 906 via one or more lead conductors (not shown). The one or more lead conductors each extend within elongate lead body 968 to provide the electrical connection between an electrode of one or more electrodes 906 and an electrode contact of the one or more electrode contacts. In one embodiment, stimulation lead 908 is an implantable lead, such as an implantable lead of the same type potentially used in the implantable system potentially received by the patient (e.g., any lead of lead system 208 or 508 or any of lead 408A, 408B, 608A, 608B, and 708). One example of such an implantable lead includes a linear array of electrodes disposed on the lead. During the neurostimulation trial, a portion of stimulation lead including lead distal end 967 are percutaneously introduced into the patient and temporarily placed in the patient. In another embodiment, stimulation lead 908 is a percutaneous lead that is similar to the implantable lead but made for temporary use. Materials for stimulation lead 908 are selected to make the lead compatible with one or more sterilization processes. Such one or more sterilization processes are required for preparing stimulation lead 908 for use with the patient.

Sensing reference electrode 960 is used to provide a reference voltage for sensing the one or more signals using sensing ETS 934. In the illustrated embodiment, sensing reference electrode 960 is suitable for attachment to the patient's skin. When such skin attachment is undesirable (e.g., because it is inconvenient for the patient and/or difficult to maintain a reliable electrical connection over the duration of the neurostimulaton trial), an implantable sensing reference electrode can be provided, as further discussed with reference to FIGS. 10-13.

Sensing wire 962 has a wire distal end 961 connected to sensing referenced electrode 960, a wire proximal end 963 including a wire connector 965 for connecting to cable assembly 972, and an elongate wire body 964 coupled between wire distal end 961 and wire proximal end 963. Wire connector 965 includes a sensing reference electrode contact electrically connected to sensing reference electrode 960. A wire conductor extending within elongate wire body 964 provides the electrical connection between sensing reference electrode 960 and the sensing reference electrode contact.

Sensing ETS 934 can delivering the neurostimulation energy and sense the one or more signals using one or more electrodes 906 and sensing reference electrode 960. Sensing ETS 934 includes an ETS connector 984 to provide for electrical connections to stimulation lead 908 and sensing wire 962 through cable assembly 972. ETS connector 984 can be constructed as a single connector with multiple electrical contacts or multiple connectors. In the illustrated embodiment, ETS connector 984 includes a reference contact 985 and two sensing and stimulation (SENS/STIM) contacts 986 (SENS/STIM 1) and 987 (SENS/STIM 2). Reference contact 985 is for the electrical connection to sensing wire 962 through cable assembly 972. Sensing and stimulation contacts 986 and 987 can each provide for the electrical connection(s) to a stimulation lead, such as stimulation lead 908, through cable assembly 972. Sensing and stimulation contacts 986 and 987 can each includes a multi-contact group allowing for separate electrical connections each for an electrode of multiple electrodes on a stimulation lead. In each of FIGS. 9-13, a neurostimulation trial system that can accommodate two stimulation leads such as stimulation lead 908, with one stimulation lead used, is illustrated as a specific example. Various embodiments of the present subject matter can accommodate and use any number of stimulation leads as practically needed for the neurostimulation trial (e.g., the same number of stimulation leads used in the implantable system evaluated for the patient).

Cable assembly 972 can provide electrical connections between sensing ETS 934 and stimulation lead 908 and an electrical connection between sensing ETS 934 and sensing wire 962. The electrical connections between sensing ETS 934 and stimulation lead 908 allow the neurostimulation energy to be transmitted from ETS connector 984 to lead connector 970 and allow the sensed one or more signals to be transmitted from lead connector 970 to ETS connector 984. The electrical connection between sensing ETS 934 and sensing wire 962 allows sensing ETS 934 to receive the reference voltage from wire connector 965. Cable assembly 972 can represent an example of the interface between ETS 634 and leads 608A and 608B and sensing wire 662 in system 600, which as illustrated in FIG. 6 includes extension cable 636 and external cable 638.

Cable assembly 972 can include a cable connector 973 (also known as an operation room cable connector) and a cable 978 (also known as an operation room cable). In the illustrated embodiment, cable connector 973 includes two sensing and stimulation (SENS/STIM) contacts 975 and 976 each to contact lead connector 970 of a stimulation lead such as stimulation lead 908. In various embodiments, cable connector 973 includes any number of sensing and stimulation contacts 975 and 976 that is needed for the neurostimulation trial. Cable connector 973 further includes a reference contact 974 to contact wire connector 965 of sensing wire 962. Sensing and stimulation contacts 975 and 976 and reference contact 974 can be configured in various ways for providing the required electrical connections. For example, sensing and stimulation contacts 975 and 976 and reference contact 974 can include physically separated connectors each to mate one of lead connector 970 or wire connector 965. Alternatively, sensing and stimulation contacts 975 and 976 and reference contact 974 can be physically integrated into a single connector. Cable 978 has a cable distal end 979 connected to cable connector 973, a cable proximal end 981 including a device connector 982 to be connected to sensing ETS 934, and an elongate cable body coupled between cable distal end 979 and cable proximal end 981. Cable 978 includes cable conductors allowing for the transmission of the neurostimulation energy from ETS connector 984 to cable connector 973 and allowing for the transmission of the sensed one or more signals from cable connector 973 to ETS connector 984. In one embodiment, cable distal end 979 can be detached from cable connector 973, such that cable 978 and cable connector 973 are separate devices that can be detachably connected. In another embodiment, cable distal end 979 is permanently affixed to cable connector 973, such that cable assembly 972 includes an integrated single device.

Cable assembly 972 can represent an example of a connection system configured to be placed outside the patient, to mate lead connector 970, to mate wire connector 965, and to provide electrical connections between lead connector 970 and sensing ETS 934 and between wire connector 965 and sensing ETS 934. In various embodiments, the connection system can include any structure providing for necessary electrical connections between lead connector 970 and circuitry of sensing ETS 934 and between wire connector 965 and circuitry of sensing ETS 934 to allow for the percutaneously delivery of neurostimulation energy to the patient and the sensing of one or more signal from the patient. In various embodiments, the connection system is external to sensing ETS 934. In various other embodiments, the connection system is included in sensing ETS 934. In various embodiments, the connection system is affixed to or otherwise integrated with sensing ETS 934. In various other embodiments, the connection system can be detachably connected to sensing ETS 934.

Figure 10:
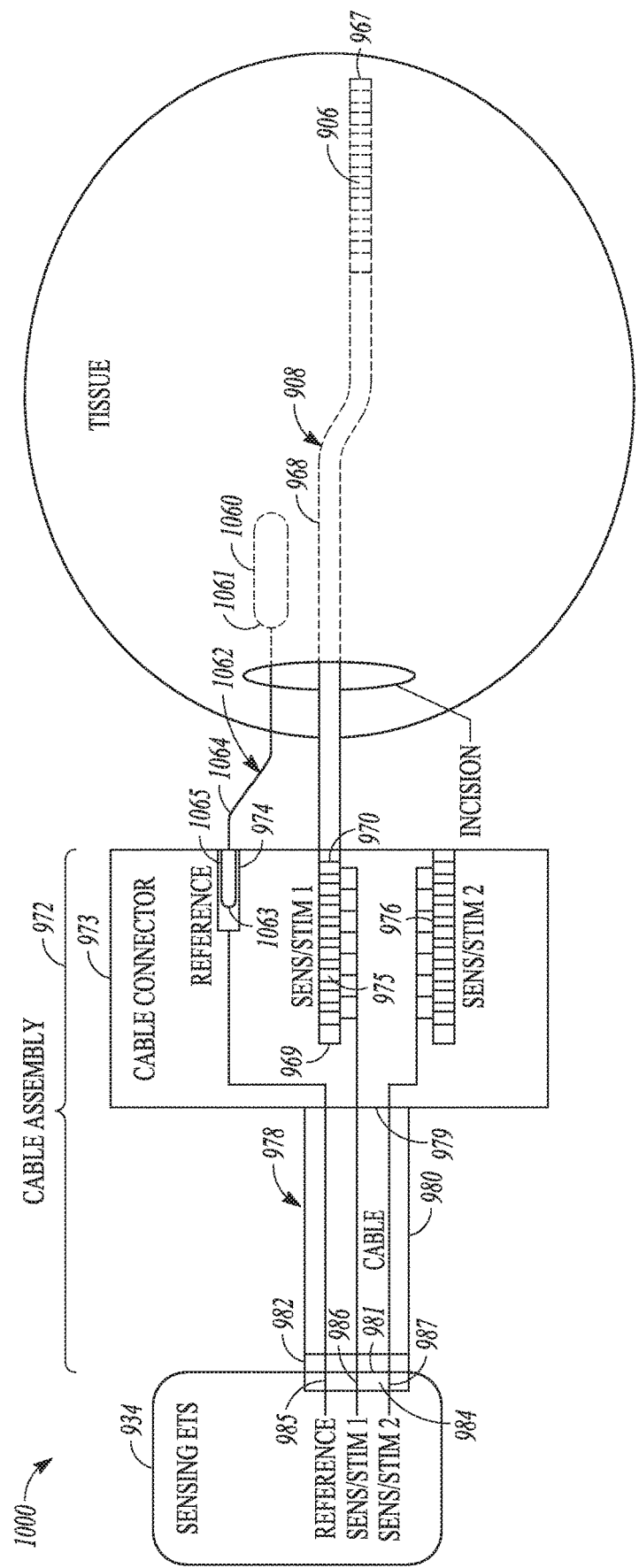
FIG. 10 illustrates an embodiment of portions of a neurostimulation trial system with an implantable sensing reference electrode.

FIG. 10 illustrates an embodiment of portions of a neurostimulation trial system 1000. System 1000 includes the elements and connections of system 900 except for that sensing reference electrode 960 with sensing wire 962 is replaced by a sensing reference electrode 1060 with a sensing wire 1062. Sensing reference electrode 1060 is an implantable sensing reference electrode made of biocompatible materials suitable for subcutaneous placement in the patient, with one or more electrode contacts made of electrically conductive and biocompatible material such as platinum.

Sensing wire 1062 has a wire distal end 1061 connected to sensing referenced electrode 1060, a wire proximal end 1063 including a wire connector 1065 for connecting to cable assembly 972, and an elongate wire body 1064 coupled between wire distal end 1061 and wire proximal end 1063. Wire connector 1065 includes a sensing reference electrode contact electrically connected to sensing reference electrode 1060. A wire conductor extending within elongate wire body 1064 provides the electrical connection between sensing reference electrode 1060 and the sensing reference electrode contact.

Sensing reference electrode 1060 can be inserted into the tissue through the incision made for inserting the portion of stimulation lead 908 including lead distal end 967 into the tissue. Then sensing reference electrode 1060 is subcutaneously placed to provide sensing ETS 934 with the reference voltage for sensing the one or more signals during the neurostimulation trial.

Materials for sensing reference electrode 1060, elongate wire body 1064, and wire connector 1065 are selected to be compatible with one or more sterilization processes. Such one or more sterilization processes are required for preparing stimulation lead 908 and sensing reference electrode 1060 with sensing wire 1062 for use with the patient.

Figure 11:
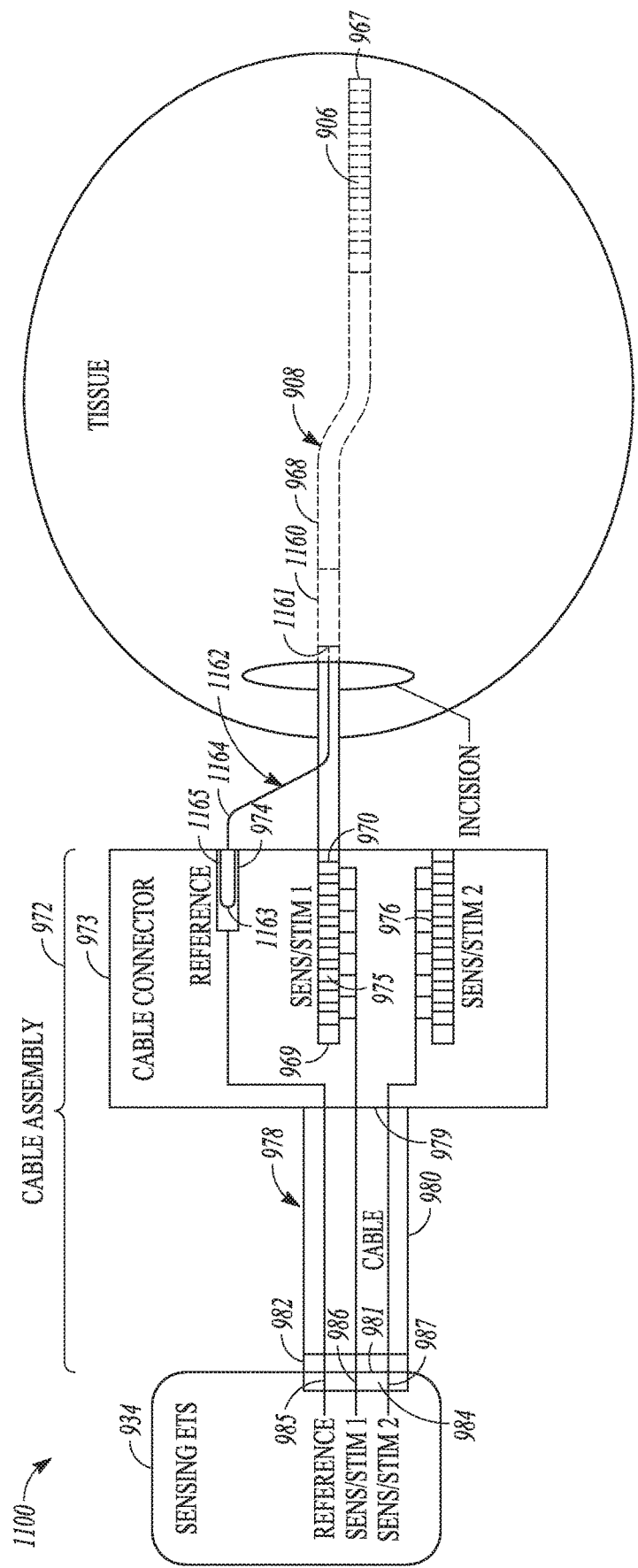
FIG. 11 illustrates an embodiment of portions of a neurostimulation trial system with a sensing reference electrode integrated into a stimulation lead.

FIG. 11 illustrates an embodiment of portions of a neurostimulation trial system 1100. System 1100 includes the elements and connections of system 900 except for that sensing reference electrode 960 with sensing wire 962 is replaced by a sensing reference electrode 1160 with a sensing wire 1162. Sensing reference electrode 1160 is an implantable sensing reference electrode made of biocompatible materials suitable for subcutaneous placement in the patient, with one or more electrode contacts made of electrically conductive and biocompatible material such as platinum.

Sensing reference electrode 1160 is integrated into lead elongate body 968 of lead 908, for example as a ring electrode, and positioned such that when one or more electrodes 906 are placed in the intended site, sensing reference electrode 1160 is in a subcutaneous location suitable for providing the reference voltage for sensing the one or more signals from the patient. In various embodiments, the integration of sensing reference electrode 1160 into stimulation lead 908 does not substantially change the size of stimulation lead 908 (e.g., diameter of lead elongate body 968 when measured with sensing reference electrode 1160).

Sensing wire 1162 has a wire distal end 1161 connected to sensing referenced electrode 1160, a wire proximal end 1163 including a wire connector 1165 for connecting to cable assembly 972, and an elongate wire body 1164 coupled between wire distal end 1161 and wire proximal end 1163. Wire connector 1165 includes a sensing reference electrode contact electrically connected to sensing reference electrode 1160. A wire conductor extending within elongate wire body 1164 provides the electrical connection between sensing reference electrode 1160 and the sensing reference electrode contact. In some embodiments, at least a portion of sensing wire 1162 can be integrated into stimulation lead 908. For example, sensing wire 1162 can be fully integrated into stimulation lead 908, with wire connector 1165 integrated into lead connector 970. Sensing wire 1162 can also be partially integrated into stimulation lead 908, with wire connector 1165 being separate from lead connector 970. Sensing wire 1162 can also be separate from stimulation lead 908, with only wire distal end 1161 connected to sensing reference electrode 1160. Wire distal end 1161 can be releasably connected to sensing reference electrode 1160, if desirable, for example when stimulation lead 908 is intended to be used as part of a permanently or chronically implanted system that may be used to treat the patient as a result of the neurostimulation trial.

Sensing reference electrode 1160 is to be inserted into the tissue with stimulation lead 908 including lead distal end 967 being inserted into the tissue. Then sensing reference electrode 1160 is subcutaneously placed to provide sensing ETS 934 with the reference voltage for sensing the one or more signals during the neurostimulation trial.

Materials for sensing reference electrode 1160, elongate wire body 1164, and wire connector 1165 are selected to be compatible with one or more sterilization processes. Such one or more sterilization processes are required for preparing stimulation lead 908 with sensing reference electrode 1160 and sensing wire 1162 for use with the patient.

Figure 12:
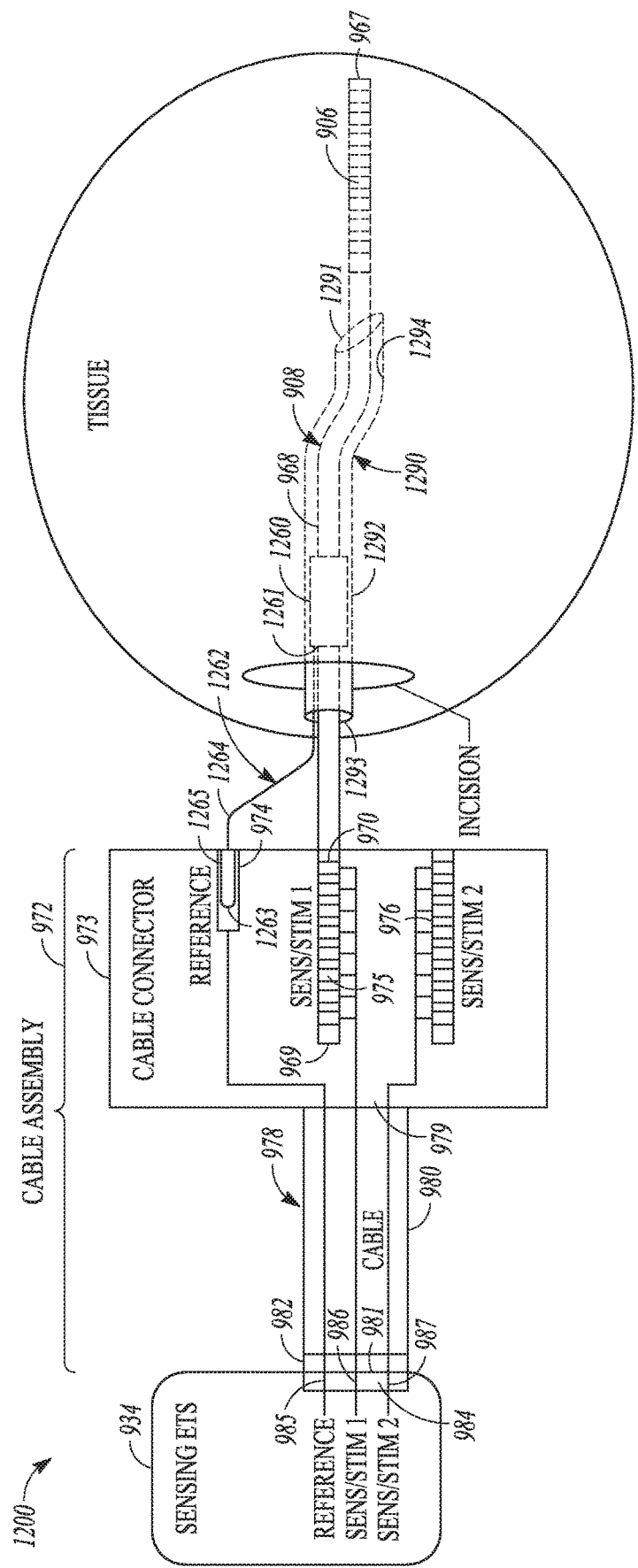
FIG. 12 illustrates an embodiment of portions of a neurostimulation trial system with a sensing reference electrode attached to a stimulation lead.

FIG. 12 illustrates an embodiment of portions of a neurostimulation trial system 1200. System 1200 includes the elements and connections of system 900 except for that sensing reference electrode 960 with sensing wire 962 is replaced by a sensing reference electrode 1260 with a sensing wire 1262. Sensing reference electrode 1260 is an implantable sensing reference electrode made of biocompatible materials suitable for subcutaneous placement in the patient, with one or more electrode contacts made of electrically conductive and biocompatible material such as platinum.

Sensing reference electrode 1260 is attached to lead elongate body 968 of lead 908 and positioned such that when one or more electrodes 906 are placed in the intended site, sensing reference electrode 1260 is in a subcutaneous location suitable for providing the reference voltage for sensing the one or more signals from the patient. In one embodiment, sensing reference electrode 1260 is detachably attached to lead elongate body 968. In another embodiment, sensing reference electrode 1260 is permanently affixed to lead elongate body 968.

Sensing wire 1262 has a wire distal end 1261 connected to sensing referenced electrode 1260, a wire proximal end 1263 including a wire connector 1265 for connecting to cable assembly 972, and an elongate wire body 1264 coupled between wire distal end 1261 and wire proximal end 1263. Wire connector 1265 includes a sensing reference electrode contact electrically connected to sensing reference electrode 1260. A wire conductor extending within elongate wire body 1264 provides the electrical connection between sensing reference electrode 1260 and the sensing reference electrode contact. In some embodiments, at least a portion of sensing wire 1262 can be also attached to stimulation lead 908. For example, a portion of sensing wire 1262 can be attached to stimulation lead 908, with wire connector 1265 being separate from lead connector 970. Sensing wire 1262 can also be separate from stimulation lead 908, with only wire distal end 1261 connected to sensing reference electrode 1260. Wire distal end 1161 can be releasably connected to sensing reference electrode 1160, if desirable, for example when stimulation lead 908 is intended to be used as part of the implantable system that may be used to treat the patient as a result of the neurostimulation trial.

Also shown in FIG. 12 is a lead introducer 1290 that can be used to assist with the insertion of the portions of stimulation lead 908 into the patient. Lead introducer 1290 includes an introducer distal end 1291 to enter the tissue of the patient, an introducer proximal end 1293, and an elongate introducer body 1292 coupled between introducer distal end 1291 and introducer proximal end 1293. A lumen 1294 extends within elongate introducer body 1292 from an introducer distal opening at or near introducer distal end 1291 and an introducer proximal opening at or near introducer proximal end 1293. Lumen 1294 can accommodate a portion of stimulation lead 908 and can allow lead distal end 967 to enter the introducer primary opening and exit from the introducer distal opening. In one embodiment, introducer distal end 1291 includes a sharp tip to pierce the tissue. In one embodiment, lead introducer 1290 is in a form of a hollow needle. In various embodiments, lead introducer 1290 is to be removed from the tissue after stimulation lead 908 is placed and before the neurostimulation energy is delivered and the one or more signals are sensed.

Sensing reference electrode 1260 is to be inserted into the tissue with stimulation lead 908 including lead distal end 967 being inserted into the tissue using lead introducer 1290. After lead introducer 1290 is removed from the tissue, sensing reference electrode 1260 contacts the tissue, providing sensing ETS 934 with the reference voltage for sensing the one or more signals during the neurostimulation trial. Thus, sensing reference electrode 1260 when attached on lead elongate body 968 and a portion of sensing wire 1262 are configured to fit through lumen 1294 to allow for the insertion of the portions of stimulation lead 908 into the tissue and the removal of lead introducer 1290 from the tissue. In one embodiment, sensing reference electrode 1260 and lumen 1294 have sizes allowing for slipping lead introducer 1290 off over stimulation lead 908 and sensing wire 1262 (including passing lead proximal end 969 and wire proximal end 1263 through lumen 1294). In another embodiment, lead introducer 1290 includes at least a portion having peel-off capability to allow for removal from stimulation lead 908 and sensing wire 1261 without passing lead proximal end 969 and wire proximal end 1263 through lumen 1294).

Materials for sensing reference electrode 1260, elongate wire body 1264, and wire connector 1265, as well as materials for lead introducer 1290, are selected to be compatible with one or more sterilization processes. Such one or more sterilization processes are required for preparing stimulation lead 908, sensing reference electrode 1260 with sensing wire 1262, and lead introducer 1290 for use with the patient.

Figure 13:
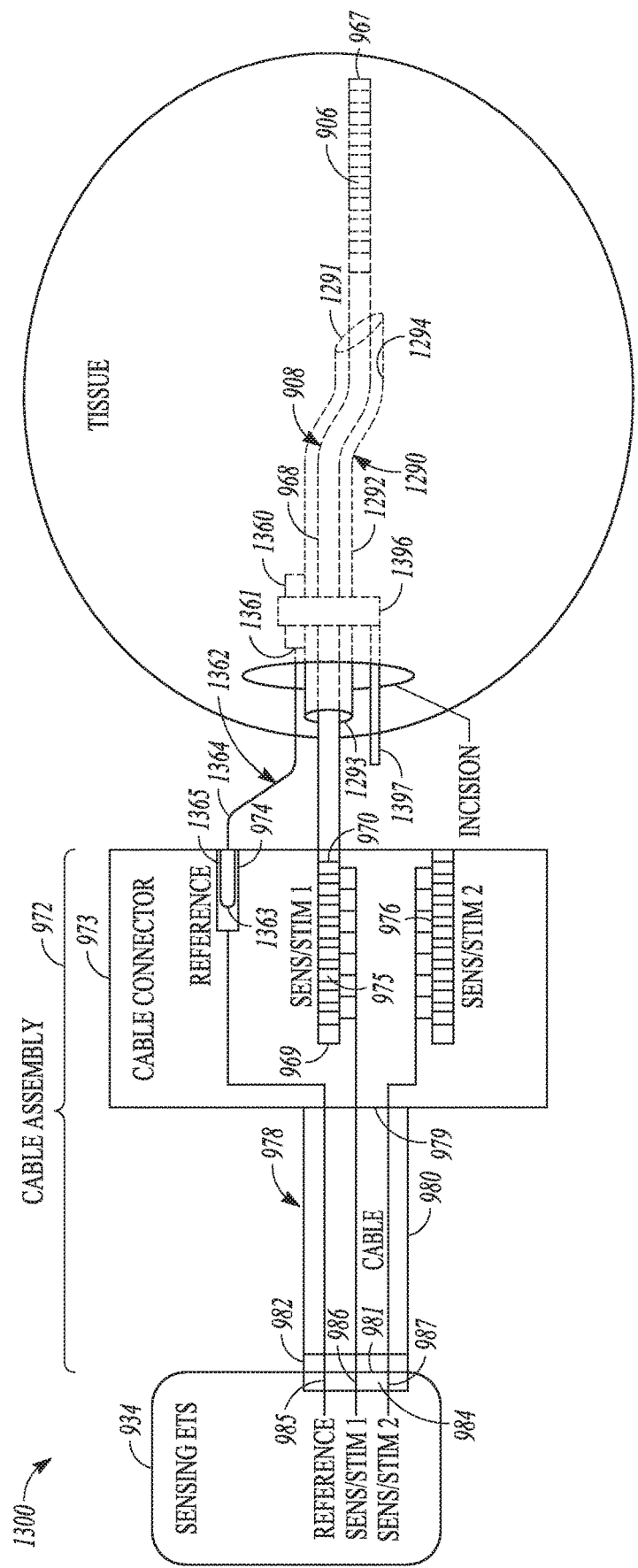
FIG. 13 illustrates an embodiment of portions of a neurostimulation trial system with a sensing reference electrode attached to a lead introducer.

FIG. 13 illustrates an embodiment of portions of a neurostimulation trial system 1300. System 1300 includes the elements and connections of system 900 except for that sensing reference electrode 960 with sensing wire 962 is replaced by a sensing reference electrode 1360 with a sensing wire 1362. Sensing reference electrode 1360 is an implantable sensing reference electrode made of biocompatible materials suitable for subcutaneous placement in the patient, with one or more electrode contacts made of electrically conductive and biocompatible material such as platinum. Sensing reference electrode 1360 is detachably attached to lead introducer 1290 in a manner allowing it to be positioned in a subcutaneous location suitable for providing the reference voltage for sensing the one or more signals from the patient after lead introducer is removed from the tissue. In the illustrated embodiment, sensing reference electrode 1360 is detachably attached to elongate introducer body 1292 of lead introducer 1290 using a releasable clip 1396 and a release handle 1397. Releasable clip 1396 allows sensing reference electrode 1360 to be detached from elongate introducer body 1292 after sensing reference electrode 1360 is in place and before lead introducer 1290 is removed from the tissue. Release handle 1397 can be used to release sensing reference electrode 1360 from releasable clip 1396.

Sensing wire 1362 has a wire distal end 1361 connected to sensing referenced electrode 1360, a wire proximal end 1363 including a wire connector 1365 for connecting to cable assembly 972, and an elongate wire body 1364 coupled between wire distal end 1361 and wire proximal end 1363. Wire connector 1365 includes a sensing reference electrode contact electrically connected to sensing reference electrode 1360. A wire conductor extending within elongate wire body 1364 provides the electrical connection between sensing reference electrode 1360 and the sensing reference electrode contact.

Sensing reference electrode 1360 is to be inserted into the tissue with a substantial portion of lead introducer 1290 including introducer distal end 1291 being inserted into the tissue. After lead introducer 1290 is removed from the tissue, sensing reference electrode 1260 contacts the tissue, providing sensing ETS 934 with the reference voltage for sensing the one or more signals during the neurostimulation trial.

Materials for sensing reference electrode 1360, elongate wire body 1364, and wire connector 1365, as well as materials for releasable clip 1396 and release handle 1397, are selected to be compatible with one or more sterilization processes. Such one or more sterilization processes are required for preparing stimulation lead 908, sensing reference electrode 1360 with sensing wire 1362, lead introducer 1290, releasable clip 1396, and release handle 1397 for use with the patient.

Figure 14:
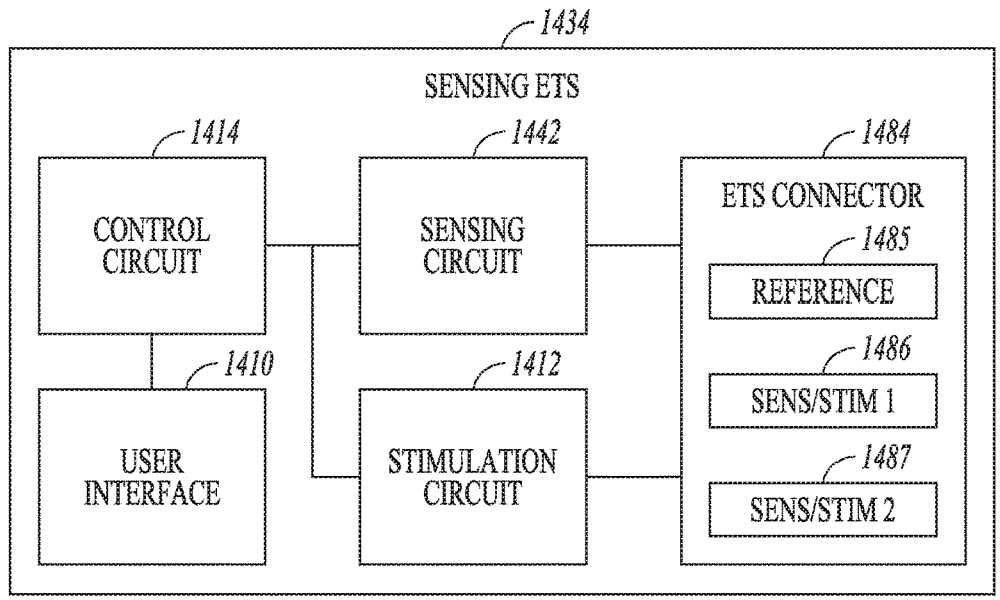
FIG. 14 illustrates an embodiment of an external trial stimulator (ETS) with sensing capabilities for use in a neurostimulation trial system, such as the neurostimulation trial system of any of FIGS. 9-13.

FIG. 14 illustrates an embodiment of a sensing ETS 1434, which can represent an example of ETS 634 or 934. Sensing ETS 1434 has sensing capabilities allowing for sensing of one or more signals from the patient during a neurostimulation trial for the patient. Sensing ETS 1434 includes a sensing circuit 1442, a stimulation circuit 1412, a control circuit 1414, a user interface 1410, and an ETS connector 1484.

Sensing circuit 1442 can sense one or more signals from the patient using one or more sensing electrodes, such as selected from one or more electrodes 906. Stimulation circuit 1412 deliver the neurostimulation energy to the patient using one or more stimulation electrodes, such as selected from one or more electrodes 906. Control circuit 1414 can control the sensing of the one or more signals by sensing circuit 1442 and control the delivery of the neurostimulation energy from stimulation 1412. User interface 1410 can allow a user to control the sensing of the one or more signal and/or the delivery of the neurostimulation energy and/or present information to the user. The presented information can include, but are not limited to, parameters controlling the sensing of the one or more signal and/or the delivery of the neurostimulation energy and/or the sensed one or more signals. In some embodiments, the presented information can further include, for example, parameters derived from the sensed one or more signals, and/or instructions for the user to conduct the neurostimulation trial.

ETS connector 1484 can provide for electrical connections to the sensing and stimulation electrode(s) and the sensing reference electrode. In the illustrated embodiment, ETS connector 1484 includes a reference contact 1485 for the electrical connection to the sensing reference electrode, a first sensing and stimulation contact 1486 (SENS/STIM 1), and a second sensing and stimulation contact 1487 (SENS/STIM 2) for use in a neurostimulation trial system such as system 900, 1000, 1100, 1200, or 1300 as illustrated in FIGS. 9, 10, 11, 12, and 13, respectively. Sensing and stimulation contacts 1486 and 1487 can each includes a multi-contact group allowing for separate electrical connections each for an electrode of multiple electrodes on a stimulation lead. In various embodiments, any one or more sensing and stimulation contacts can be included to accommodate the number of stimulation leads needed for the neurostimulation trial.

Figure 15:
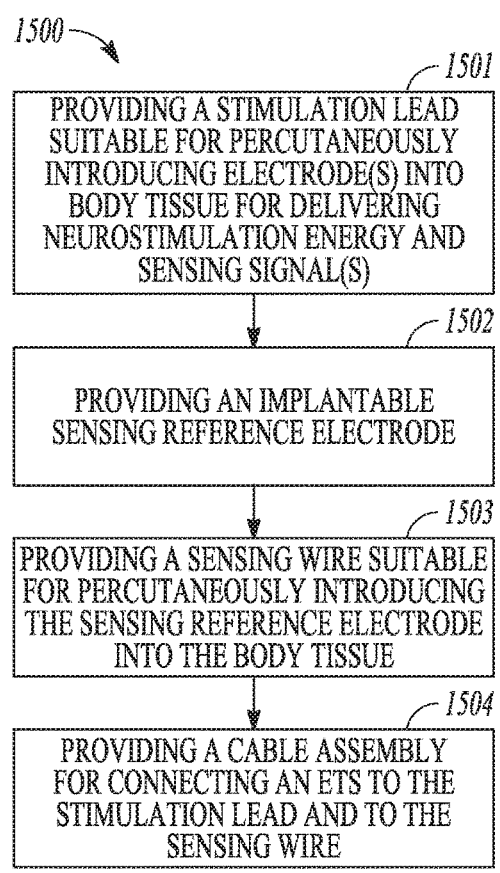
FIG. 15 illustrates an embodiment of a method for providing an interface between a patient and an ETS, such as the ETS of FIG. 14

FIG. 15 illustrates an embodiment of a method 1500 for providing an interface between a patient and an ETS during a neuromodulation trial. The neuromodulation trial uses a trial system that emulates functions of an implantable system, including delivering neurostimulation energy to the patient and sensing one or more signals from the patient, for purposes including determining whether the implantable system can provide the patient with a suitable therapy and/or determining parameters for the therapy. The trial system includes a test device placed externally to the patient and including sensing and stimulation capabilities, such as sensing ETS 934. Method 1500 can be performed using a suitable trial system selected from systems 900, 1000, 1100, 1200, and 1300.

At 1501, an elongate stimulation lead suitable for percutaneously introducing one or more electrodes into the patient for delivering the neurostimulation energy and sensing the one or more signals is provided. The stimulation lead includes a lead distal end including the one or more electrodes and a lead proximal end including a lead connector having one or more electrode contacts electrically connected to the one or more electrodes. In one embodiment, the elongate stimulation lead is an implantable lead that is suitable for chronic or permanent implantation in the patient. In one embodiment, the elongate stimulation lead is a percutaneous lead that is similar to the implantable lead but suitable for temporary use such as use for the duration of the neurostimulation trial.

At 1502, a sensing reference electrode suitable for placing in the patient is provided. In one embodiment, the sensing reference electrode is an implantable electrode suitable for subcutaneous placement in the patient and connected to a sensing wire. In another embodiment, the sensing reference electrode is integrated into the stimulation lead in a location that is subcutaneous when the one or more electrodes of the stimulation lead are in place. In another embodiment, the sensing reference electrode is attached (e.g., detachably attached) to the stimulation lead in a location that is subcutaneous when the one or more electrodes of the stimulation lead are in place. In another embodiment, a lead introducer suitable for percutaneously introducing the stimulation lead for placing the one or more electrode in the patient is provided. The lead introducer includes an introducer distal end suitable for entering the patient, an introducer proximal end, an elongate introducer body coupled between the introducer distal end and the introducer proximal end, and a lumen extending within the introducer body from an introducer distal opening at or near the introducer distal end and an introducer proximal opening at or near the introducer proximal end. The lumen has a size accommodating a portion of the stimulation lead and allowing the lead distal end to enter the introducer primary opening and exit from the introducer distal opening. The sensing reference electrode is detachably attached to the lead introducer, and can be detached from the lead introducer before the lead introducer is removed from the patient. This can be achieved, for example, by providing a releasable clip to attach the sensing reference electrode to the lead introducer and a release handle coupled to the releasable clip. The sensing reference electrode is detached from the lead introducer by releasing the releasable clip using the release handle.

At 1503 an elongate sensing wire suitable for percutaneously introducing the sensing reference electrode into the patient to provide a reference for sensing the one or more signals is provided. The sensing wire includes a wire distal end connected to the sensing referenced electrode and a wire proximal end including a wire connector having a sensing reference electrode contact electrically connected to the sensing reference electrode. In some embodiments, the wire distal end is detachably connected to the sensing referenced electrode.

At 1504, a cable assembly for connecting the test device to the stimulation lead and to the sensing wire is provided. The cable assembly is suitable for use externally to the patient and includes a cable connector and a cable connected to the cable connector and providing electrical connections between the cable connector and the test device. The cable connector is suitable for mating the lead connector and mating the wire connector, and a cable.

With all the system elements provided by method 1500 are interconnected as illustrated in one or more of FIGS. 10-13, the neurostimulation energy can be delivered, and the one or more signals can be sensed, according to the requirements of the neurostimulation trial. An example of such a neurostimulation trial performed for evaluating a SCS therapy includes percutaneously introducing the stimulation lead to place the one or more electrodes subcutaneously over the spinal cord of the patient, sensing the one or more signals using the one or more electrodes placed subcutaneously over the spinal cord, and processing the sensed one or more signals using the test device. The example can further include (for example, after a sensing period) generating the neurostimulation energy using the test device and delivering the neurostimulation energy to the spinal cord using the one or more electrodes.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A method for sensing one or more signals from a patient, the method comprising:
   providing an elongate stimulation lead configured for percutaneously introducing one or more electrodes into the patient for delivering neurostimulation energy to the patient and sensing the one or more signals from the patient, the stimulation lead including a lead distal end including the one or more electrodes and a lead proximal end including a lead connector having one or more electrode contacts electrically connected to the one or more electrodes;
   providing a sensing reference electrode configured for placing in the patient;
   providing an elongate sensing wire configured for percutaneously introducing the sensing reference electrode into the patient to provide a reference for sensing the one or more signals, the sensing wire at least partially separated from the stimulation lead and including a wire distal end connected to the sensing reference electrode and a wire proximal end including a wire connector having a sensing reference electrode contact electrically connected to the sensing reference electrode;
   connecting each of the lead connector and the wire connector to a test device placed externally to the patient, the test device configured for delivering the neurostimulation energy and sensing the one or more signals; and
   sensing the one or more signals from the patient using the test device, the one or more electrodes of the stimulation lead, and the sensing reference electrode.

2. The method of claim 1, wherein connecting each of the lead connector and the wire connector to the test device comprises:
   providing a cable assembly including:
      a cable connector configured to mate the lead connector and to mate the wire connector; and
      a cable connected to the cable connector and providing electrical connections between the cable connector and the test device; and
   connecting each of the lead connector and the wire connector to the test device using the cable assembly.

3. The method of claim 2, wherein the cable connector comprises physically separated connectors each configured to mate one of the lead connector and the wire connector.

4. The method of claim 2, wherein the cable connector comprises a single connector configured to mate both the lead connector and the wire connector.

5. The method of claim 2, wherein the cable comprises a distal end connected to the cable connector, a proximal end including a device connector configured to be detachably connected to the test device, and an elongate body coupled between the distal end and the proximal end.

6. The method of claim 1, wherein providing the elongate stimulation lead comprises providing an implantable lead.

7. The method of claim 1, further comprising attaching sensing reference electrode to the stimulation lead.

8. The method of claim 1, further comprising integrating the sensing reference electrode into the stimulation lead.

9. The method of claim 1, further comprising providing a lead introducer configured for percutaneously introducing the stimulation lead for placing the one or more electrode in the patient, the lead introducer including an introducer distal end configured to enter the patient, an introducer proximal end, an elongate introducer body coupled between the introducer distal end and the introducer proximal end, and a lumen extending within the introducer body from an introducer distal opening at or near the introducer distal end and an introducer proximal opening at or near the introducer proximal end, the lumen configured to accommodate a portion of the stimulation lead and to allow the lead distal end to enter the introducer primary opening and exit from the introducer distal opening.

10. The method of claim 9, further comprising detachably attach the sensing reference electrode to the lead introducer.

11. The method of claim 10, further comprising detaching the sensing reference electrode from the lead introducer after the stimulation lead is percutaneously introduced using the lead introducer.

12. The method of claim 11, further comprising providing a releasable clip to attach the sensing reference electrode to the lead introducer and a release handle coupled to the releasable clip, and wherein detaching the sensing reference electrode from the lead introducer comprises releasing the releasable clip using the release handle.

13. The method of claim 1, further comprising:
generating the neurostimulation energy using the test device;
delivering the neurostimulation energy to the spinal cord using the one or more electrodes of the stimulation lead; and
sensing the one or more signals while delivering the neurostimulation energy.

14. The method of claim 1, further comprising:
generating the neurostimulation energy using the test device;
delivering the neurostimulation energy to the patent for a deep brain therapy using the one or more electrodes of the stimulation lead; and
sensing the one or more signals while delivering the neurostimulation energy.

15. The method of claim 1, wherein connecting each of the lead connector and the wire connector to the test device comprises using a connection system configured to be placed externally to the patient.

16. The method of claim 15, wherein connecting each of the lead connector and the wire connector to the test device comprises using a connection system within the testing device.

17. The method of claim 15, wherein connecting each of the lead connector and the wire connector to the test device comprises using a connection system external to the testing device.

18. The method of claim 17, wherein connecting each of the lead connector and the wire connector to the test device comprises using a connection system configured to be detachably connected to the testing device.

19. The method of claim 18, wherein sensing the one or more signals comprises sensing one or more biopotential signals each indicative of a response of the patient to delivery of the neurostimulation during the trial of the neurostimulation therapy.

20. The method of claim 1, wherein sensing the one or more signals comprises sensing one or more biopotential signals each indicative of a condition of the patient that is treated by a neurostimulation therapy during a trial of the neurostimulation therapy.

\* \* \* \* \*